United States Patent
Asirvatham

(10) Patent No.: US 11,571,377 B2
(45) Date of Patent: *Feb. 7, 2023

(54) SURFACTANTS FOR USE IN PERSONAL CARE AND COSMETIC PRODUCTS

(71) Applicant: AdvanSix Resins & Chemicals LLC, Parsippany, NJ (US)

(72) Inventor: Edward Asirvatham, Chatham, NJ (US)

(73) Assignee: AdvanSix Resins & Chemicals LLC, Parsippany, NJ (US)

( * ) Notice: Subject to any disclaimer, the term of this patent is extended or adjusted under 35 U.S.C. 154(b) by 84 days.

This patent is subject to a terminal disclaimer.

(21) Appl. No.: 17/118,304

(22) Filed: Dec. 10, 2020

(65) Prior Publication Data

US 2021/0186842 A1 Jun. 24, 2021

Related U.S. Application Data

(60) Provisional application No. 62/950,378, filed on Dec. 19, 2019.

(51) Int. Cl.
| | |
|---|---|
| *A61Q 5/12* | (2006.01) |
| *A61Q 5/02* | (2006.01) |
| *A61Q 5/00* | (2006.01) |
| *A61Q 19/00* | (2006.01) |
| *A61Q 11/00* | (2006.01) |
| *A61K 8/00* | (2006.01) |
| *A61K 8/58* | (2006.01) |
| *A61K 8/04* | (2006.01) |
| *A61K 8/19* | (2006.01) |
| *A61K 8/21* | (2006.01) |
| *A61K 8/44* | (2006.01) |
| *A61Q 1/10* | (2006.01) |
| *A61Q 19/10* | (2006.01) |
| *C07F 7/08* | (2006.01) |

(52) U.S. Cl.
CPC .............. *A61K 8/585* (2013.01); *A61K 8/046* (2013.01); *A61K 8/19* (2013.01); *A61K 8/21* (2013.01); *A61K 8/44* (2013.01); *A61Q 1/10* (2013.01); *A61Q 5/02* (2013.01); *A61Q 5/12* (2013.01); *A61Q 11/00* (2013.01); *A61Q 19/10* (2013.01); *C07F 7/0838* (2013.01); *A61K 2800/48* (2013.01); *A61K 2800/596* (2013.01)

(58) Field of Classification Search
CPC ............ A61Q 5/00; A61Q 5/512; A61Q 5/02; A61Q 5/12; A61Q 19/00; A61Q 11/00; A61K 8/585; A61K 8/89; A61K 8/25; A61K 2800/10

See application file for complete search history.

(56) References Cited

U.S. PATENT DOCUMENTS

| | | | |
|---|---|---|---|
| 3,624,120 A | 11/1971 | Yetter | |
| 3,929,678 A | 12/1975 | Laughlin et al. | |
| 5,041,590 A | 8/1991 | Snow | |
| 5,162,155 A | 11/1992 | Berndt et al. | |
| 5,707,550 A * | 1/1998 | Glover | A61K 8/585 516/55 |
| 6,013,683 A | 1/2000 | Hill et al. | |
| 7,622,512 B2 | 11/2009 | Schorzman et al. | |
| 10,053,619 B2 | 8/2018 | Saboowala et al. | |
| 11,008,348 B2 | 5/2021 | Asirvatham et al. | |
| 2007/0099805 A1 | 5/2007 | Phenis et al. | |
| 2007/0104778 A1 | 5/2007 | Zeng et al. | |
| 2007/0142583 A1* | 6/2007 | Schorzman | C08F 230/08 526/279 |
| 2008/0152540 A1 | 6/2008 | Schorzman et al. | |
| 2010/0063310 A1 | 3/2010 | Knepper et al. | |
| 2010/0215959 A1 | 8/2010 | Jonschker et al. | |
| 2011/0158927 A1* | 6/2011 | Viravau | A61K 8/463 424/70.13 |
| 2012/0093746 A1 | 4/2012 | Moriya | |
| 2013/0130508 A1 | 5/2013 | Wu et al. | |
| 2018/0057732 A1 | 3/2018 | Babcock et al. | |
| 2018/0362716 A1 | 12/2018 | Okamura | |
| 2019/0112549 A1 | 4/2019 | Bauer et al. | |
| 2020/0148831 A1 | 5/2020 | Okamura | |
| 2020/0231608 A1 | 7/2020 | Okamura | |
| 2021/0054002 A1 | 2/2021 | Asirvatham et al. | |
| 2021/0187110 A1 | 6/2021 | Asirvatham | |
| 2021/0187460 A1 | 6/2021 | Asirvatham | |
| 2021/0188882 A1 | 6/2021 | Asirvatham | |

(Continued)

FOREIGN PATENT DOCUMENTS

| | | |
|---|---|---|
| CN | 102614808 A | 8/2012 |
| CN | 104826140 A | 8/2015 |

(Continued)

OTHER PUBLICATIONS

International Search Report and Written Opinion received for PCT Patent Application No. PCT/US20/64345, dated Apr. 12, 2021, 9 pages.

International Search Report and Written Opinion received for PCT Patent Application No. PCT/US20/64347, dated Mar. 10, 2021, 7 pages.

International Search Report and Written Opinion received for PCT Patent Application No. PCT/US20/64684, dated Mar. 25, 2021, 14 pages.

International Search Report and Written Opinion received for PCT Patent Application No. PCT/US20/64687, dated Mar. 31, 2021, 12 pages.

(Continued)

*Primary Examiner* — Tracy Liu

(74) *Attorney, Agent, or Firm* — Faegre Drinker Biddle & Reath LLP

(57) ABSTRACT

Personal care products, such as shampoos, conditioners, hair dyes, hair removal products, cleansers, cosmetics, mascaras, and toothpastes may be formulated to include one or more surfactants, from one or more surfactant classes, such as siloxane derivatives of amino acids that have surface-active properties.

20 Claims, 7 Drawing Sheets

(56) References Cited

U.S. PATENT DOCUMENTS

| | | |
|---|---|---|
| 2021/0189292 A1 | 6/2021 | Asirvatham |
| 2021/0198555 A1 | 7/2021 | Asirvatham |
| 2021/0230194 A1 | 7/2021 | Asirvatham et al. |
| 2021/0238479 A1 | 8/2021 | Asirvatham |

FOREIGN PATENT DOCUMENTS

| | | |
|---|---|---|
| CN | 107497365 A | 12/2017 |
| CN | 107522726 A | 12/2017 |
| CN | 107602862 A | 1/2018 |
| CN | 107698615 A | 2/2018 |
| EP | 0164514 A1 | 12/1985 |
| EP | 0436359 A2 | 7/1991 |
| EP | 2024423 A2 | 2/2009 |
| EP | 2458622 A2 | 5/2012 |
| GB | 1429143 A | 3/1976 |
| GB | 1470250 A | 4/1977 |
| GB | 1473201 A | 5/1977 |
| GB | 1473202 A | 5/1977 |
| KR | 10-2015-0108143 A | 9/2015 |
| TW | 201307372 A | 2/2013 |
| WO | 00/26206 A1 | 5/2000 |
| WO | 02/46517 A1 | 6/2002 |
| WO | 2007/075320 A2 | 7/2007 |
| WO | 2007/141565 A2 | 12/2007 |
| WO | WO-2008114232 A2 * | 9/2008 ............... A61K 8/40 |
| WO | 2009/085297 A2 | 7/2009 |
| WO | 2015/041214 A1 | 3/2015 |
| WO | 2016/191148 A1 | 12/2016 |
| WO | 2021/003455 A1 | 1/2021 |
| WO | 2021/034550 A1 | 2/2021 |

OTHER PUBLICATIONS

International Search Report and Written Opinion received for PCT Patent Application No. PCT/US20/64692, dated Apr. 7, 2021, 9 pages.
International Search Report and Written Opinion received for PCT Patent Application No. PCT/US20/66027, dated Apr. 7, 2021, 12 pages.
International Search Report and Written Opinion received for PCT Patent Application No. PCT/US20/66031, dated Apr. 8, 2021, 12 pages.
International Search Report and Written Opinion received for PCT Patent Application No. PCT/US2020/045797, dated Oct. 26, 2020, 11 pages.
Stanbro et al., "Cationic silicones for use in contact lens application", Polymer Preprints, 51(2), 2010, pp. 305-306.

* cited by examiner

SURFACTANTS FOR USE IN PERSONAL CARE AND COSMETIC PRODUCTS

CROSS-REFERENCE TO RELATED APPLICATION

This application claims priority to U.S. Provisional Application No. 62/950,378, filed Dec. 19, 2019, the disclosure of which is herein incorporated by reference in its entirety.

FIELD

The present disclosure pertains to surfactants for use in personal care and cosmetics products. Such surfactants may include siloxane derivatives of amino acids wherein the siloxane derivatives have surface-active properties.

BACKGROUND

Surfactants (molecules with surface-active properties) are widely used in commercial applications in formulations ranging from detergents to hair care products to cosmetics. Compounds with surface-active properties are used as soaps, detergents, lubricants, wetting agents, foaming agents, and spreading agents, among others. In personal care cleansing products (e.g., shampoos, body washes, facial cleansers, liquid hand soaps, etc.) the surfactant is often the most important component because it provides many of the cleansing attributes of the composition.

Surfactants may be uncharged, zwitterionic, cationic, or anionic. Although in principle any surfactant class (e.g., cationic, anionic, nonionic, amphoteric) is suitable in cleansing or cleaning applications, in practice many personal care cleansers and household cleaning products are formulated with a combination of two or more surfactants from two or more surfactant classes.

Often, surfactants are amphiphilic molecules with a relatively water-insoluble hydrophobic "tail" group and a relatively water-soluble hydrophilic "head" group. These compounds may adsorb at an interface, such as an interface between two liquids, a liquid and a gas, or a liquid and a solid. In systems comprising relatively polar and relatively non-polar components the hydrophobic tail preferentially interacts with the relatively non-polar component(s) while the hydrophilic head preferentially interacts with the relatively polar component(s). In the case of an interface between water and oil, the hydrophilic head group preferentially extends into the water, while the hydrophobic tail preferentially extends into the oil. When added to a water-gas interface, the hydrophilic head group preferentially extends into the water, while the hydrophobic tail preferentially extends into the gas. The presence of the surfactant disrupts at least some of the intermolecular interaction between the water molecules, replacing at least some of the interactions between water molecules with generally weaker interactions between at least some of the water molecules and the surfactant. This results in lowered surface tension and can also serve to stabilize the interface.

At sufficiently high concentrations, surfactants may form aggregates which serve to limit the exposure of the hydrophobic tail to the polar solvent. One such aggregate is a micelle. In a typical micelle the molecules are arranged in a sphere with the hydrophobic tails of the surfactant(s) preferentially located inside the sphere and the hydrophilic heads of the surfactant(s) preferentially located on the outside of the micelle where the heads preferentially interact with the more polar solvent. The effect that a given compound has on surface tension and the concentration at which it forms micelles may serve as defining characteristics for a surfactant.

SUMMARY

The present disclosure provides personal care products, such as shampoos, conditioners, hair dyes, hair removal products, cleansers, cosmetics, mascaras, dental prosthetic cleansers, and toothpastes. These products may be formulated to include one or more surfactants from one or more surfactant classes disclosed herein.

The present disclosure provides surfactants for personal care products in the form of siloxane derivatives of amino acids that have surface-active properties. The amino acids may be naturally occurring or synthetic amino acids, or they may be obtained via ring-opening reactions of molecules such as lactams, for instance caprolactam. The amino acids may be functionalized with different types of siloxane groups to form compounds with surface-active properties. Characteristically, these compounds may have low critical micelle concentrations (CMC) and/or the ability to reduce the surface tension of a liquid.

The present disclosure provides a formulation for a shampoo, comprising at least one surfactant of Formula I,

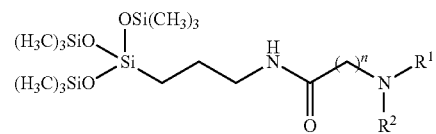

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a soil penetration agent; a foaming agent; a foam booster; a pH stabilizer; at least one thickener; a fragrance, and water.

The present disclosure further provides a formulation for a hair conditioner, comprising at least one surfactant of Formula I,

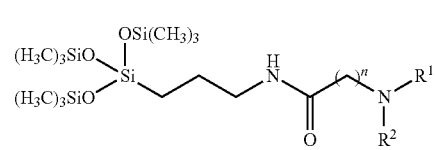

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a fatty component; at least one thickening agent; at least one emulsifier; a foaming agent; at least one clay; at least one thickener; a fragrance; and water.

The present disclosure further provides a formulation for a cleanser, comprising at least one surfactant of Formula I,

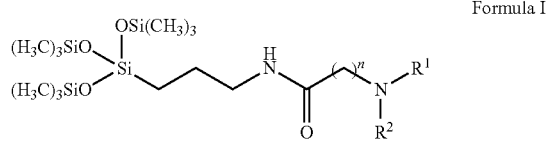

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one humectant; at least one conditioner; at least one solvent; at least one water-soluble polymer; at least one water-soluble solvent; at least one fatty components; a hydrophobicity modifier; and water.

The present disclosure also provides a formulation for a mascara, comprising at least one surfactant of Formula I,

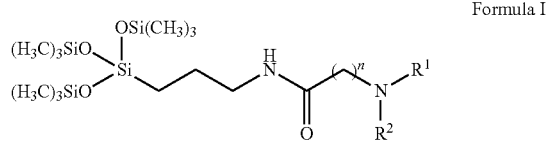

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one fatty component; at least one rheology modifier; at least one emulsifier; at least one polymer; a pigment; and water.

The present disclosure further provides a formulation for a toothpaste, comprising at least one surfactant of Formula I,

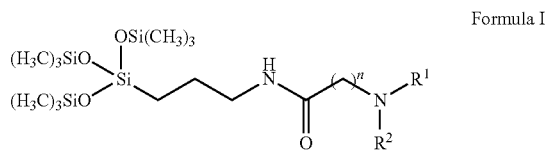

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one basic amino acid; a calcium carbonate; a fluoride ion source; a flavoring agent; and water.

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
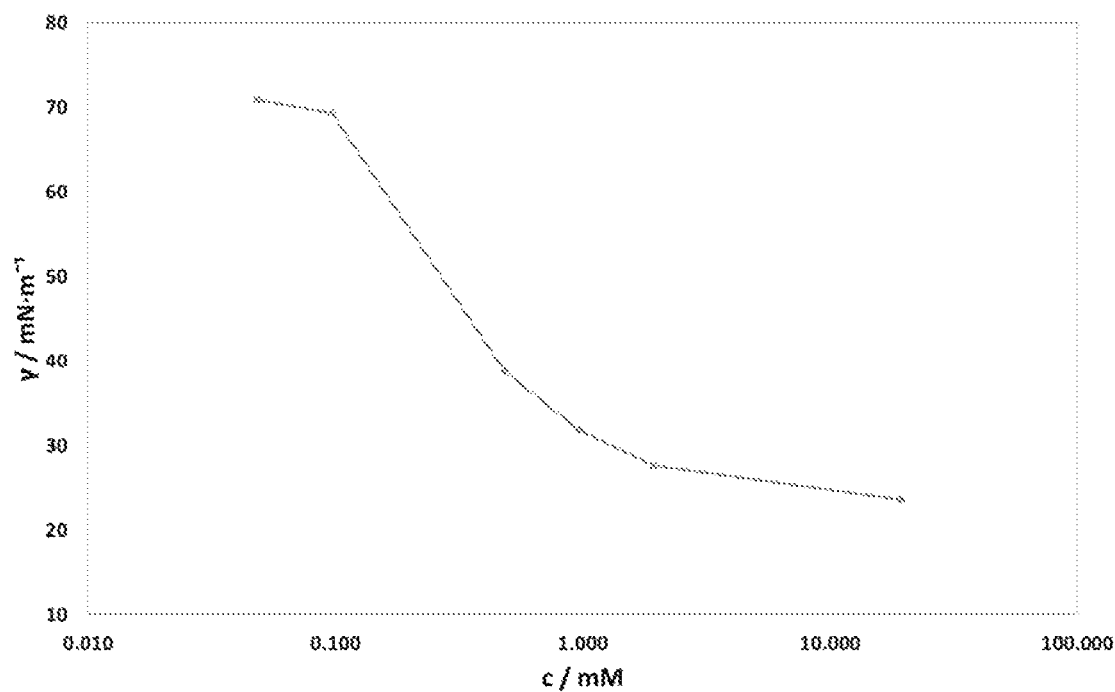
FIG. 1 shows a plot of surface tension versus concentration for Surfactant 2, with a chloride counterion measured at pH=7 as described in Example 1b.

As used herein, the phrase "within any range using these endpoints" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the word "alkyl" means any saturated carbon chain, which may be a straight or branched chain.

As used herein, the phrase "surface-active" means that the associated compound is able to lower the surface tension of the medium in which it is at least partially dissolved, and/or the interfacial tension with other phases, and, accordingly, may be at least partially adsorbed at the liquid/vapor and/or other interfaces. The term "surfactant" may be applied to such a compound.

With respect to the terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

The present disclosure provides formulations of personal care products, such as shampoos, conditioners, hair dyes, hair removal products, cleansers, cosmetics, mascaras, and toothpastes.

I. Shampoo Formulations

Shampoo compositions may comprise combinations of surfactants and conditioning agents. Such products comprise one or more surfactants in combination with a conditioning agent such as silicone, hydrocarbon oil, fatty esters, or combinations thereof. In shampoo combinations including conditioning agents, the deposition of the conditioning agent may be improved by the inclusion of certain cationic deposition polymers. These cationic deposition polymers may be natural polymers, such as cellulosic or guar polymers that have been modified with cationic substituents.

For example, a formulation for shampoo may include: a) a cosmetically acceptable medium; b) from about 1 wt. % to about 60 wt. % of at least one of the surfactants of the present disclosure; and c) from about 0.01 wt. % to about 10 wt. % of a water-soluble cationically modified starch polymer, wherein said water-soluble cationically modified starch polymer has a molecular weight from about 1,000 to about 200,000 and a charge density from about 0.7 meq/g to about 7 meq/g.

Additionally, the shampoo formulation may further comprise from about 0.01 wt. % to about 10 wt. % of one or more oily conditioning agents.

The present disclosure is also directed to a method of treating hair or skin comprising the steps of applying the shampoo formulation as described above to the hair or skin and rinsing the hair or skin.

The combination of the cationically modified starch polymer with the one or more surfactants of the present disclosure in personal care compositions provides enhanced deposition of conditioning agents to hair and/or skin without reducing cleansing performance.

1. Cosmetically Acceptable Medium

The shampoo formulations of the present disclosure comprise a cosmetically acceptable medium. The level and species of the medium are selected according to the compatibility with other components and other desired characteristic of the product. Generally, the cosmetically acceptable medium is present in an amount of about 20 wt. % or greater, about 30 wt. % or greater, about 40 wt. % or greater, about 50 wt. % or greater, or about 55 wt. % or less, about 60 wt. % or less, about 70 wt. % or less, about 80 wt. % or less, about 90 wt. % or less, or about 99 wt. % or less, by weight of the composition. A cosmetically acceptable medium may be selected such that the composition of the present invention may be in the form of, for example, a pourable liquid, a gel, a paste, a dried powder, or a dried film.

Cosmetically acceptable mediums useful in the shampoo formulations of the present disclosure include water and water solutions of lower alkyl alcohols. Lower alkyl alcohols useful herein are monohydric alcohols having 1 to 6 carbons, and preferably are selected from ethanol and isopropanol.

2. Surfactant

The shampoo formulations of the present invention comprise one or more surfactants, also referred to as the surfactant system. The surfactant system is included to provide cleaning performance to the composition. The surfactant system comprises at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable surfactants for use in the shampoo formulations of the present disclosure include one or more surfactants and/or co-surfactants of Formula I,

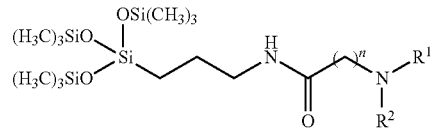

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The concentration of the surfactant system in the shampoo formulation should be sufficient to provide the desired cleaning and lather performance, and generally ranges from about 5 wt. % or greater, about 10 wt. % or greater, about 15 wt. % or greater, about 20 wt. % or greater, or about 25 wt. % or less, about 30 wt. % or less, about 40 wt. % or less, about 45 wt. % or less, or about 50 wt. % or less, or within any range using these endpoints, such as about 8 wt. % to about 30 wt. %, or about 10 wt. % to about 25 wt. %, by weight of the composition.

3. Conditioning Agents

The shampoo formulations of the present disclosure may include oily conditioning agents. Such conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the shampoo formulations of the present disclosure may comprise a water-insoluble, water-dispersible, non-volatile, liquid that forms emulsified, liquid particles. Suitable oily conditioning agents are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents may be present at a concentration a range of about 0.01 wt. % or greater, about 1 wt. % or greater, about 5 wt. % or greater, or about 6 wt. % or less, about 8 wt. % or less, or about 10 wt. % or less, or within any range using these endpoints, such as about 0.05 wt. % to about 5 wt. %, by weight of the composition.

The ratio of oily conditioning agent to cationic hydrolyzed starch polymer may be at least about 2:1.

Other conditioning agents, such as quaternary ammonium compounds, may also be included in the shampoo formulation. Suitable quaternary ammonium compounds for use as conditioning agents in the personal care compositions of the present invention include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

Further examples of useful quaternary ammonium surfactants include, but are not limited to, Quaternium-16, Quaternium-27, Quaternium-30, Quaternium-52, Quaternium-53, Quaternium-56, Quaternium-60, Quaternium-61, Quaternium-62, Quaternium-63, Quaternium-71 Quaternium-33, Quaternium-43, isostearamidopropyl ethyldimonium ethosulfate, Quaternium-22 and Quaternium-26, or combinations thereof, as designated in the CTFA Dictionary.

4. Cationically Modified Polymer

The shampoo formulations of the present disclosure comprise water-soluble cationically modified starch polymers. As used herein, the term "cationically modified starch" refers to a starch to which a cationic group is added prior to degradation of the starch to a smaller molecular weight, or to a starch to which a cationic group is added after modification of the starch to a desired molecular weight. The definition of the term "cationically modified starch" also includes amphoterically modified starch. The term "amphoterically modified starch" refers to a starch hydrolysate to which a cationic group and an anionic group are added.

The shampoo formulations of the present disclosure comprise cationically modified starch polymers at a range of about 0.01 wt. % or greater, about 1 wt. % or greater, about 5 wt. % or greater, or about 6 wt. % or less, about 8 wt. % or less, or about 10 wt. % or less, or within any range using these endpoints, such as about 0.05 wt. % to about 5 wt. %, by weight of the composition.

The cationically modified starch polymers for use in the shampoo formulations of the present disclosure have a molecular weight from about 1,000 or greater to about 200,000 or less. In one example, the cationically modified starch polymers have a molecular weight from about 5,000 to about 100,000. As used herein, the term "molecular weight" refers to the weight average molecular weight. The weight average molecular weight may be measured by gel permeation chromatography ("GPC") using an Alliance HPLC (Waters 2695 Separation Module) with two hydrogel columns in series (Waters Ultrahydrogel Linear 6-13 um, 7.8×300 nm GPC column, part number 011545) at a column temperature of 30° C. and at a flow rate of 0.9 ml/min, and using a Viscotek Model 300 TDA (triple detector array), light scattering detector (single angle, 90°), viscosity detector, and refractive index detector, all at detector temperatures of 30° C., with a method created by using pullulan narrow standard P-800 from American Polymer Standards Corporation ($M_w$=788,000), with an injection volume of 25 to 100 μl, and using a do/dc of 0.147. Additional details on measuring the weight average molecular weight according to a GPC method are described in U.S. Publication No. 2003/0154883 A1, entitled "Non-Thermoplastic Starch Fibers and Starch Composition for Making Same."

The shampoo formulations of the present disclosure include cationically modified starch polymers which have a charge density from about 0.7 meq/g or greater to about 7 meq/g or less. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. The cationic groups may be added to the starch prior to degradation to a smaller molecular weight or the cationic groups may be added after such modification.

The cationically modified starch polymers for use in the shampoo formulations of the present disclosure may comprise maltodextrin. Thus, in one example, the cationically modified starch polymers may be further characterized by a Dextrose Equivalance ("DE") value of less than about 35, and more preferably from about 1 or more to about 20 or less. The DE value is a measure of the reducing equivalence of the hydrolyzed starch referenced to dextrose and expressed as a percent (on dry basis). Starch completely hydrolyzed to dextrose has a DE value of 100, and unhydrolyzed starch has a DE value of 0. A suitable assay for DE value includes one described in "Dextrose Equivalent", *Standard Analytical Methods of the Member Companies of the Corn Industries Research Foundation,* 1st ed., Method E-26. Additionally, the cationically modified starch polymers of the present invention may comprise a dextrin. Dextrin is typically a pyrolysis product of starch with a wide range of molecular weights.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

In one example, cationically modified starch polymers are selected from degraded cationic maize starch, cationic tapioca, cationic potato starch, and mixtures thereof. In another example, cationically modified starch polymers are cationic corn starch.

The starch, prior to degradation or after modification to a smaller molecular weight, may comprise one or more additional modifications. For example, these modifications may include cross-linking, stabilization reactions, phophorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

5. Other Additives

The shampoo formulation may include other additives, such as soil penetration agents, foaming agents, foam boosters, thickeners, fragrances, pigments, and/or preservatives.

Individual concentrations of such additional components may range from about 0.001 wt. % or greater, about 0.01 wt. % or greater, about 1 wt. % or greater, about 5 wt. % or greater, or about 6 wt. % or less, about 8 wt. % or less, or about 10 wt. % or less, or within any range using these endpoints, such as about 0.05 wt. % to about 5 wt. %, by weight of the composition.

The pH of the shampoo formulation, measured neat, is preferably from about 3 to about 9, more preferably from about 4 to about 8. Buffers and other pH-adjusting agents can be included to achieve the desirable pH.

The shampoo formulations of the present disclosure may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the shampoo formulation, and should not otherwise unduly impair product stability, aesthetics or performance.

The shampoo formulations of the present disclosure may also contain one or more opacifying agents. Opacifying agents are typically used in cleansing compositions to impart desired aesthetic benefits to the shampoo formulation, such as color or pearlescence. In the shampoo formulations of the present disclosure, it is preferable to incorporate no more than about 20 wt. % or less, more preferably no more than about 10 wt. % or less, and even more preferably no more than 2 wt. % or less, by weight of the composition, of opacifying agents.

Suitable opacifying agents include, for example, fumed silica, polymethylmethacrylate, micronized TEFLON®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above-mentioned powders may be surface treated with lecithin, amino acids, mineral oil, silicone oil, or various other agents either alone or in combination, which coat the powder surface and render the particles hydrophobic in nature.

The shampoo formulations of the present disclosure may further comprise a suspending agent at concentrations effective for suspending water-insoluble material in dispersed form in the compositions or for modifying the viscosity of the shampoo formulation. Such concentrations generally range from about a range of about 0.01 wt. % or greater, about 1 wt. % or greater, about 5 wt. % or greater, or about 6 wt. % or less, about 8 wt. % or less, or about 10 wt. % or less, or within any range using these endpoints, such as about 0.05 wt. % to about 5 wt. %, by weight of the composition.

Suspending agents useful herein include anionic polymers and nonionic polymers. Useful herein are vinyl polymers such as cross-linked acrylic acid polymers with the CTFA name Carbomer.

The shampoo formulations of the present disclosure may contain one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

The shampoo formulations of the present disclosure also may contain one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

The shampoo formulations of the present disclosure may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The shampoo formulations of the present disclosure may contain foaming agents or foam boosters, such as ammonium lauryl sulfate, sodium lauryl sulfate, ammonium lauryl ether sulfate, and cocamidopropyl betaine.

The shampoo formulations of the present disclosure may include thickeners, such as xanthan gum and acrylate copolymers.

The shampoo formulations of the present disclosure may contain a mono- or divalent salt such as sodium chloride.

The shampoo formulations of the present disclosure may also contain chelating agents.

The shampoo formulations of the present disclosure may further comprise materials useful for hair loss prevention and hair growth stimulants or agents.

6. Method of Making

The shampoo formulations of the present disclosure, in general, may be made by mixing the ingredients together at either room temperature or at elevated temperature, e.g., about 72° C. Heat only needs to be used if solid ingredients are in the composition. The ingredients are mixed at the batch processing temperature. Additional ingredients, including electrolytes, polymers, fragrance, and particles, may be added to the product at room temperature.

7. Method of Treating Hair

The shampoo formulations of the present disclosure are used in a conventional manner for cleansing and conditioning hair. Generally, a method of treating hair comprises applying the shampoo formulation of the present disclosure to the hair. More specifically, an effective amount of the shampoo formulation is applied to the hair, which has preferably been wetted with water, and then the shampoo formulation is rinsed off. Such effective amounts generally range from about 1 g to about 50 g, preferably from about 1 g to about 20 g. Application to the hair typically includes working the shampoo formulation through the hair such that most or all of the hair is contacted with the shampoo formulation.

This method for treating the hair comprises the steps of: (a) applying an effective amount of the shampoo formulation to the hair, and (b) rinsing the applied areas of hair with water. These steps can be repeated as many times as desired to achieve the desired cleansing and conditioning benefit.

For some forms of the shampoo formulation of the present disclosure, the shampoo formulation may be packaged in a pump-dispenser bottle or in an aerosol container. In other useful forms, the shampoo formulation may be dried to a film or a powder, or it may be applied to a substrate which is then used for application to the hair.

II. Conditioner Formulations

The present disclosure provides formulations of hair conditioners. The conditioner formulations of the present disclosure may provide durable styling and conditioning benefits, impart frizz control and curl definition, and improve the health and manageability of the hair. After hair is optionally cleansed, for example, with a shampoo, a conditioner may be applied to the hair to impart a multitude of benefits to the hair. For example, the hair may be initially treated (after being optionally cleansed) with a rinse-off conditioner, which provides conditioning and detangling properties to the hair.

A non-limiting example of a rinse-off conditioner may include at least 4 wt. % or more of a natural fatty component, the natural fatty component comprising one or more solid, semi-solid, or liquid natural fatty compounds; at least 1 wt. % or more of one or more surfactants selected from one or more surfactant classes; one or more nonionic thickening agents; one or more emulsifiers; one or more mineral based clays; and water.

1. Fatty Compound

The rinse-off conditioner may include both a natural solid or semi-solid fatty compound (e.g., a wax or butter) and a natural liquid oil. For example, a combination of Shea butter and sunflower seed oil can be particularly useful. An appropriate viscosity for the rinse-off conditioner may be attained instead using a natural fatty component, surfactants, and nonionic thickening agents. For instance, nonionic polysaccharide thickening agents (e.g., sclerotium gum) can be particularly useful.

The rinse-off conditioning mask includes a high amount (typically at least 4 or 5 wt. %) of a natural fatty component. The natural fatty component may include both a natural solid or semi-solid fatty compound (e.g., a wax or butter) and natural liquid oil. For purposes of the present disclosure, a solid or semi-solid fatty compound is a fatty substance having a melting of 31° C. or higher. An oil, on the other hand, is a fatty substance having a melting point below 31° C. Accordingly, an oil will be a liquid at room temperature. Reference to a total amount of a natural fatty component does not necessarily indicate an absence of a non-natural fatty component in the rinse-off conditioner. In other words, in some cases, the rinse-off conditioner may include one or more non-natural fatty compounds in addition to the compounds of the natural fatty component. Nonetheless, it may be desirable to exclude non-natural fatty compounds in order to derive a natural product.

The term "natural" as used herein in the present disclosure refers to natural-based ingredients such as plant- or vegetable-derived ingredients, for example, the natural fatty component or the solid or semi-solid natural fatty compounds or the natural oils of the disclosure. The term "non-natural" as used herein in the present disclosure refers to ingredients that are not natural-based and may include alkane or hydrocarbon or synthetic oils such as mineral oil or silicone oil.

The total amount of natural fatty component may be about 4 wt. % or greater, about 5 wt. % or greater, about 10 wt. % or greater, or about 15 wt. % or less, about 20 wt. % or less, or about 25 wt. % or less, or any range combination using these endpoints, based on the total weight of the rinse-off conditioner.

Non-limiting examples of solid or semi-solid fatty compounds include those from plants, animals, and mineral sources, for example, Shea butter, bayberry wax, bees wax, illipe butter, paraffin wax, hard tallow, lanolin, kokum butter, Sal butter, spermaceti, murumuru seed butter, beeswax, ceresin wax, cocoa butter, jojoba wax, candelilla wax, palm butter, carnauba wax, esparto wax, shellac wax, sugarcane wax, lignite wax, ouricouri wax, rice bran wax, castor wax, Montan wax, sugar cane wax, rice bran wax, sunflower wax, and a mixture thereof. In some cases, Shea butter may be particularly useful.

Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof. In some cases, sunflower oil may be particularly useful.

2. Surfactant

The conditioner formulations of the present invention comprise one or more surfactants, also referred to as the surfactant system. The surfactant system is included to deposit onto hair, thus smoothing the cuticle and creating softness. The surfactant system comprises at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof.

Suitable surfactants for use in the conditioner formulations of the present disclosure include one or more surfactants and/or co-surfactants of Formula I,

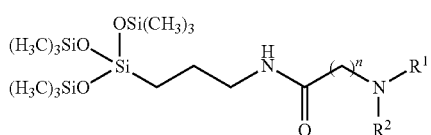

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The total amount of the one or more surfactants in the rinse-off conditioner may vary but it typically at least 1 wt. % or greater, based on the total weight of the rinse-off conditioning mask. In some cases, the total amount of the one or more surfactants may be about 1 wt. % or greater, about 2 wt. % or greater, about 4 wt. % or greater, about 6 wt. % or greater, or about 8 wt. % or less, about 10 wt. % or less, about 12 wt. % or less, or about 15 wt. % or less, or within any range included within these endpoints, such as about 1 wt. % to about 8 wt. %, about 1 wt. % to about 6 wt. %, about 1 wt. % to about 5 wt. %, or about 2 wt. % to about 10 wt. %.

3. Thickening Agents

The rinse-off conditioner may include one or more nonionic thickening agents. All thickening referred to throughout the disclosure may also be referred to as "rheology modifiers," "thickening compounds," "thickeners," "gelling agents," and the like. Nonionic thickening agents include nonionic guar gums, sclerotium gum, biopolysaccharide gums of microbial origin, gums derived from plant exudates, celluloses, in particular hydroxypropylcelluloses or hydroxyethylcelluloses, pectins, and mixtures thereof.

Suitable nonionic thickening agents may include celluloses modified with groups comprising at least one fatty chain. Examples of such modified celluloses may include: hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product NATROSOL PLUS GRADE 330 CS (016 alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol, Further suitable nonionic thickening agents may include hydroxypropyl guars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc.

Still other suitable nonionic thickening agents may include copolymers of vinylpyrrolidone and of fatty-chain hydrophobic monomers; copolymers of 01-06 alkyl methacrylates or acrylates and of amphiphilic monomers comprising at least one fatty chain; polyurethane polyethers comprising in their chain both hydrophilic blocks usually of polyoxyethylenated nature and hydrophobic blocks, which may be aliphatic sequences alone and/or cycloaliphatic and/or aromatic sequences; or polymers with an aminoplast ether backbone containing at least one fatty chain.

In some instances, the nonionic thickening agents may be chosen from the group consisting of polysaccharides and associative polymers. In some cases, the preferred nonionic thickening agents are sclerotium gum, guar gums, hydroxyalkyl celluloses optionally modified with a hydrophobic group, such as hydroxyethylcelluloses, hydroxymethylcelluloses optionally modified with a hydrophobic group, and inulins optionally modified with a hydrophobic group. In some cases, sclerotium gum is particularly useful.

The total amount of the one or more nonionic thickening agents may vary but is typically about 0.1 wt. % or greater, about 0.5 wt. % or greater, about 1 wt. % or greater, about 2 wt. % or greater, or about 4 wt. % or less, about 6 wt. % or less, about 8 wt. % or less, or within any range included by these endpoints, based on the total weight of the rinse-off conditioner.

4. Emulsifiers

The rinse-off conditioners may be in the form of an emulsion, for example, a water-in-oil emulsion. Accordingly, one or more emulsifiers may be included. Useful emulsifiers include, for example, fatty acids, fatty alcohols, esters of polyols and of a fatty acid, polyol fatty esters and fatty ethers with a branched or unsaturated chain containing from 10 to 30 carbon atoms, esters of sorbitan and a fatty acid, esters of sugar and a fatty acid, and a mixture thereof. The fatty chains in the emulsifiers may be, for example from about 8 to about 35 carbon atoms in length, and may be saturated or unsaturated, and may be optionally branched. In some cases, the fatty chains are about 10 to about 30 carbon atoms in length or about 12 to about 24 carbon atoms in length.

Non-limiting examples of emulsifiers include sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate; glyceryl behenate, glyceryl caprate, glyceryl caprylate, glyceryl caprylate/ caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, sucrose cocoate, sucrose laurate, methyl glucose sesquistearate, methyl glucose dioleate, cetyl alcohol, stearyl alcohol, cetearyl alcohol, cetyl esters, and a mixture thereof.

The total amount of the one or more emulsifiers may vary depending on the other components and their amounts in the rinse-off conditioner. Nonetheless, the total amount of the one or more emulsifiers is typically about 0.5 wt. % or greater, about 1 wt. % or greater, about 2 wt. % or greater, about 5 wt. % or greater, or about 10 wt. % or less, about 12 wt. % or less, about 14 wt. % or less, about 16 wt. % or less, or about 20 wt. %, or less, or within any range encompassed by these endpoints, based on the total weight of the rinse-off conditioner.

5. Clays

One or more mineral based clays may be included in the rinse-off conditioner. Mineral based clays may include: kaolins (e.g., the minerals kaolinite, dickite, halloysite, and nacrite); smectites, (e.g., dioctahedral smectites such as montmorillonite, nontronite and beidellite and trioctahedral smectites for example saponite); Illites (e.g., clay-micas); chlorites; and other clays types such as sepiolite and attapulgite.

The total amount of mineral based clay in the rinse-off conditioner may vary, but may typically be about 0.01 wt. % or greater, about 1 wt. % or greater, about 5 wt. % or greater, or about 6 wt. % or less, about 8 wt. % or less, or about 10 wt. % or less, or within any range using these endpoints, based on the total weight of the rinse-off conditioner.

6. Water and Water-Soluble Solvents

The total amount of water in the rinse-off conditioner may vary but is typically about 50 wt. % or greater, about 60 wt. % or greater, about 70 wt. % or greater, or about 80 wt. % or less, about 90 wt. % or less, or within any range using these endpoints, based on the total weight of the rinse-off conditioner.

Water-soluble solvents may optionally be included in the rinse-off conditioner. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, organic solvents, such as 01-4 alcohols, polyols, glycols, and a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents are chosen from polyols which include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols may also be useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2, 6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble solvents may vary but may typically be about 0.1 wt. % or greater, about 1 wt. % or greater, about 5 wt. % or greater, about 10 wt. % or greater, or about 15 wt. % or less, about 20 wt. % or less, about 25 wt. % or less, or within any range using these endpoints, based on the total weight of the rinse-off conditioner.

7. Other Additives

The conditioner formulation of the present disclosure may include other additives, such as emulsifiers, foaming agents, hydrotropes, fragrances, pigments, and stabilizers, for example.

The conditioner formulation of the present disclosure may include emulsifiers. Suitable emulsifiers may include sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate; glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, sucrose cocoate, sucrose laurate, methyl glucose sesquistearate, methyl glucose dioleate, cetyl alcohol, stearyl alcohol, cetearyl alcohol, cetyl esters, polyethylene glycol (PEG) and its derivatives, and a mixture thereof.

The conditioner formulation of the present disclosure may include foaming agents or foam boosters, such as such as ammonium lauryl sulfate, sodium lauryl sulfate, ammonium lauryl ether sulfate, and cocamidopropyl betaine.

The conditioner formulation of the present disclosure may include hydrotropes, such as benzene sulfonates, naphthalene sulfonates, short chain ($C_{1-11}$) alkyl benzene sulfonates, medium chain ($C_{6-11}$) alkyl sulfonates, medium chain ($C_{6-11}$) alkyl sulfates, alkylpolyglucosides, medium chain ($C_6$-$C_{10}$) alkyl dimethyl amine oxides, alkyl diphenyloxide disulfonates, phosphate ester hydrotropes, and medium chain ($C_{6-11}$) alkyl ether (up to 10 moles of ethylene oxide) sulfates. The cations of the hydrotropic compounds may include alkali metal, ammonium, and triethanolammonium cations.

8. Method of Use

A typical method (also referred to as a "routine") for treating hair according to the present disclosure may include an optional first step, in which the hair is cleansed, for example, with a cleansing composition such as a shampoo, and a second step, in which the hair is treated with a rinse-off conditioner, and the rinse-off conditioner is rinsed from the hair after it has remained on the hair for a sufficient amount of time.

III. Cleansers

The present disclosure further provides formulations of cleansers. These formulations may be useful for cleansing the body, especially the skin. Additionally, the cleansing formulations of the present disclosure may be useful for removing makeup from the skin. When cleansing and/or removing makeup from the skin, the cleanser formulations may be applied to the skin and rinsed from the skin with water. These cleanser formulations may be gentle to the skin and hydrate the skin during cleansing.

The cleansers of the present disclosure may include at least one nonionic surfactant, and at least one additional surfactant chosen from one or more surfactant classes, an oil agent, a water-soluble alcohol, a water-soluble polyol, at least one water-soluble polymer, a water-soluble inorganic or organic salt, and water.

1. Surfactant

The cleanser of the present disclosure may include a first surfactant chosen from nonionic surfactants, and a second surfactant, comprising one or more additional surfactants chosen from one or more surfactant classes. To provide stability to the composition, it may be preferable to use a mixture of surfactants. This allows the cleanser to be rinsed away without a remaining feel.

Suitable surfactants for use in the cleanser formulations of the present disclosure include one or more surfactants and/or co-surfactants of Formula I,

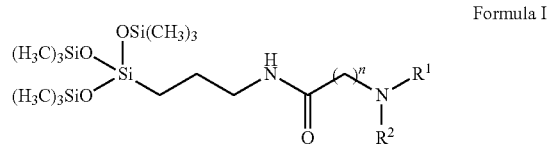

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The content of the first surfactant is about 15 wt. % or greater, about 20 wt. % or greater, or about 25 wt. % or less, about 30 wt. % or less, or within any range using these endpoints. This allows the agent being clearly rinsed away without a remaining feel. The content within this range provides improved compatibility with makeup and is capable of floating the stain, while being cleanly rinsed off without a remaining feel.

One or more surfactants chosen from one or more surfactant classes may be used for the second surfactant. The content of this second surfactant is about 1 wt. % or greater, about 5 wt. % or greater, or about 10 wt. % or less, about 15 wt. % or less, or within any range using these endpoints.

2. Oil Agent

The oil agent may comprise hydrocarbon oils; and one, two or more compound(s) selected from the group consisting of ester oils and ether oils, in which the viscosity at 30° C. is equal to or lower than 30 mPa·s. The viscosity of the oil agent may be measured by employing BM type viscometer (commercially available from TOKIMEC Co., Ltd., measurement conditions: rotor No. 1, 60 rpm, for one minute). Such oil agent of lower viscosity exhibits higher permeability to micro segments and higher solubility for the stains, so that enhanced cleansing-ability is achieved for oily makeup stains such as an oily mascara and the like. Further, such oil agent does not involve strong oily feel, and exhibits improved feel of use. It is preferable that the oil agent is liquid at 20° C., since this provides enhanced cleansing-ability for the reason described above.

Liquid oils, which are ordinarily employed for cosmetic compositions and satisfy the above-described conditions, may be employed for such oil agent. For example, liquid paraffin, liquid isoparaffin, scualane, isododecane and the like may be employed for the hydrocarbon oil of the oil agent.

Ester oils of the oil agent may include isostearic acid cholesteryl ester (cholesteryl isostearate), isopropyl palmitate, isopropyl myristate, isopropyl isostearate, octadecyl myristate, cetyl 2-ethylhexanoate, isononyl isononanoate, isotridecyl isononanoate, neopentylglycol dicaprate, glyceryl tri(2-ethylhexanoate), glyceryl tri(caprylate/caprate) and the like. In view of difficulty in precipitation of crystal, ester oils having branched alkyl chain is preferable.

Ether oils of the oil agent may include ether oils such as alkyl-1,3-dimethylbutyl ether, dioctyl ether, nonylphenyl ether and the like.

The content of the oil agent is about 10 wt. % or greater, about 15 wt. % or greater, about 20 wt. % or greater, or about 25 wt. % or less, about 30 wt. % or less, about 35 wt. % or less, about 40 wt. % or less, or within any range using these endpoints.

2. Water-Soluble Polyol

The water-soluble polyol is a compound having three or more hydroxyl group in the molecule, such as: glycerols such as glycerol, diglycerol and the like; saccharides such as sorbitol, maltitol, maltose, fructose, xylitol, maltotriose, threitol, erythritol, glucose and the like; and sugar derivatives such as methylglucoside, ethylglucoside and the like. Among these, glycerol, sorbitol and maltitol are preferable, to enhance the moisture-retention effect. Further, glycerol and sorbitol are preferable in view of the rinsing-ability. The water-soluble polyol serves as enhancing superficial hydrophobicity in the whole skin cleansing formulation.

One or more of water-soluble polyols may be employed, and it may be preferable to employ a combination of two or more compounds.

The water-soluble polyol is present in the cleanser formulation at 10 wt. % or greater, about 15 wt. % or greater, about 20 wt. % or greater, or about 25 wt. % or less, about 30 wt. % or less, about 35 wt. % or less, about 40 wt. % or less, or within any range using these endpoints.

3. Water-Soluble Alcohol

The water-soluble alcohol is a compound having one or two hydroxyl group in a molecule. Water-soluble alcohols may include: monatomic alcohols such as ethanol, propanol, isopropanol, butanol, isobutanol and the like; and glycols such as ethylene glycol, propylene glycol, diethylene glycol, dipropylene glycol, 1,3-butylene glycol, 1,4-butylene glycol, hexylene glycol, isoprene glycol and the like. Compounds having two hydroxyl groups in the molecule may be preferable, and 1,3-butylene glycol, isoprene glycol, propylene glycol and dipropyleneglycol are even more preferable, in view of their temperature stability over a wide range of temperatures.

A mixture of one or more water-soluble alcohols may be used. The water-soluble alcohol may be present in the cleanser formulation in an amount of 10 wt. % or greater, about 15 wt. % or greater, about 20 wt. % or greater, or about 25 wt. % or less, about 30 wt. % or less, or within any range using these endpoints.

The mass ratio of the water-soluble polyol to the water-soluble alcohol in the cleanser formulation is preferably 0.1 to 2.5 and is more preferably 1 to 2.5.

4. Water-Soluble Polymer

The water-soluble polymer may be composed of one, two or more of component(s) selected from water-soluble polymers containing (meth)acrylic acid as structural unit (water-soluble polymers containing structural unit derived from (meth)acrylic acid) and acryloyl methyl taurate-vinylpyrrolidone copolymers. The water-soluble polymer serves as increasing the viscosity of the skin cleansing agent composition of the present invention such that the drip of the liquid is avoided when the cleanser is coated over the skin, and such that the cleanser can be sufficiently mixed with the stains such to provide easy cleansing.

The water-soluble polymer which contains structural unit of (meth)acrylic acid may be a compound synthesized by employing (meth)acrylic acid as monomer, such as an acrylic acid-alkyl methacrylate copolymer, which is typically a cross linking-type copolymer of acrylic acid and alkyl (C10 to C30) methacrylate, and more typically the commercially available products of, for example, PEMULEN TR-1, PEMULEN TR-2, PEMULEN TR-1, PEMULEN TR-1, Carbopol ETD 2020 (commercially available from Lubrizol Advanced Materials Inc.) and the like.

The water-soluble polymer containing (meth)acrylic acid as the structural unit is preferably employed by neutralizing all of or a portion of the unit of (meth)acrylic acid with an alkali agent. The alkali agent for the neutralization is not particularly limited as long as the agent is the alkali agent that can be ordinarily blended in the cosmetic compositions, such as potassium hydroxide, sodium hydroxide and the like. One or more compounds may be employed for the alkali agent. The agent may be present at about 0.01 wt. % or greater, 0.1 wt. % or greater, 0.2 wt. % or greater, 0.4 wt. % or greater, or 0.6 wt. % or less, 0.8 wt. % or less, 1.0 wt. % or less, or within any range encompassed by these endpoints, such that the pH of the composition is 5 or greater, 6 or greater, or 7 or less, 8 or less, or 9 or less, or within any range using these endpoints.

5. Water-Soluble Inorganic and Organic Salts

The water-soluble salts may be composed of one, two or more of defined components selected from water-soluble inorganic salts and organic salts having 1 to 8 carbon atoms. Water solubility is herein as a compound of which 5 grams or more may be dissolved in 100 g of water at 20° C. The water-soluble salt of the cleanser is hydrated and dissolved, and thus superficial hydrophobicity of the whole skin cleansing agent composition is enhanced.

Suitable water-soluble inorganic salts may include metallic hydroxide of alkali metals and salts of ammonium with hydrochloric acid, sulfuric acid, nitric acid, phosphoric acid, triphosphoric acid, pyrophosphoric acid and carbonic acid; for example, chlorides such as sodium chloride, potassium chloride, magnesium chloride and the like; sulfates such as sodium sulfate, potassium sulfate, magnesium sulfate, aluminum sulfate and the like; and carbonates such as sodium carbonate, sodium hydrogen carbonate and the like.

Suitable water-soluble organic salts having 1 to 8 carbon atoms may include salts of acids such as lactic acid, succinic acid, citric acid, tartaric acid, malic acid, maleic acid, fumaric acid and the like with alkali metal, ammonium and the like, such as: monosodium citrate, disodium citrate, trisodium citrate, potassium lactate, ammonium succinate, potassium malate and the like.

6. Water

Water is present in the cleanser formulation at 5 wt. % or greater, 10 wt. % or greater, 20 wt. % or greater, or 30 wt. % or lower, 40 wt. % or lower, 50 wt. % or lower, or within any range encompassed by these endpoints, such as 5 wt. % to 50 wt. %, 10 wt. % to 30 wt. %, or 20 wt. % to 40 wt. %. This permits the cleanser to be cleanly rinsed without remaining feel while maintaining sufficient cleansing-ability.

7. Other Additives

The cleanser formulation may further contain components that are ordinarily employed for the cleansing agent, typically for example, thickening agents, disinfecting agents, moisturizing agents, humectants, colorants, antiseptic agents, feel improvers, odorants, anti-inflammatory agents, skin-lightening agents, antiperspirants, UV absorbers, antioxidants, various types of extracts and the like, may be suitably included.

IV. Mascara

The present disclosure also provides formulations of mascaras. The mascara formulation of the present disclosure provides low wax and/or wax free mascara compositions that provide good body and volume to the lashes, can be applied to lashes easily and yield smooth, homogenous layers with fewer clumps than traditional mascaras. The mascaras of the invention are also easily removed with water and experience less flaking or smudging than traditional mascaras.

The mascara formulation may be in the form of an oil-in-water emulsion (O/W). The O/W emulsions of the present disclosure comprise an oil phase (or lipophilic phase) dispersed in an aqueous phase. In such emulsions, the aqueous phase is thus the continuous phase of the composition while the oil phase is the dispersed phase of the composition. The oil phase is present in an amount ranging from about 3 wt. % or greater, about 5 wt. % or greater, about 10 wt. % or greater, about 15 wt. % or greater, about 20 wt. % or greater, about 25 wt. % or greater, or about 30 wt. % or lower, about 35 wt. % or lower, about 40 wt. % or lower, about 45 wt. % of lower, about 50 wt. % or lower, or within any range encompassed by these endpoints, by weight relative to the total weight of the composition.

The aqueous phase is present in an amount ranging from about 50 wt. % or greater, about 55 wt. % or greater, about 60 wt. % or greater, about 65 wt. % or greater, or about 70 wt. % or greater, about 75 wt. % or lower, about 80 wt. % or lower, about 85 wt. % or lower, about 90 wt. % or lower, about 95 wt. % or lower, about 97 wt. % or lower, or within any range encompassed by these endpoints, by weight relative to the total weight of the composition.

The pH of the emulsion of the invention at 25° C. ranges from about 6.5 or greater, about 7.0 or greater, about 7.5 or lower, about 8.0 or lower, about 8.5 or lower, or within any range using these endpoints. to about 8.5, most preferably about 7.3+/−0.3.

The mascara may include a liquid fatty substance, one or more surfactants chosen from one or more surfactant classes, one or more rheology modifiers or viscosity increasing agents, one or more film forming systems comprising at least one film forming polymer and at least one co-film former, and water.

1. Liquid Fatty Substance

The liquid fatty substance may be selected from cetyl PEG/PPG-10/1 dimethicone, dimethicone (and) dimethiconol, and mixtures thereof.

The liquid fatty substance may be present in the mascara formulation in an amount of about 0.1 wt. % or greater, about 1 wt. % or greater, about 5 wt. % or greater, about 10 wt. % or greater, or about 15 wt. % or less, about 20 wt. % or less, about 25 wt. % or less, about 30 wt. % or less, or within any range using these endpoints.

2. Surfactants

The mascara formulation includes one or more surfactants chosen from one or more surfactant classes, collectively referred to as the surfactant system. The surfactant system functions as an emulsifier for the O/W emulsion.

Suitable surfactants for use in the mascara formulations of the present disclosure include one or more surfactants and/or co-surfactants of Formula I,

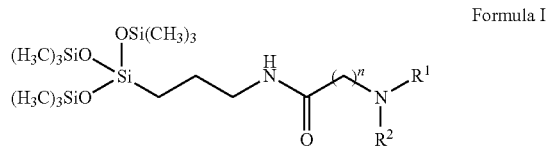

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The surfactant system is present in the mascara formulation in an amount of from about 3 wt. % or greater, about 5 wt. % or greater, about 8 wt. % or greater, or about 10 wt. % or less, about 15 wt. % or less, about 20 wt. % or less or within any range using these endpoints.

3. Rheology Modifier

The rheology modifier, or viscosity increasing agent, may be chosen from nonionic, anionic, cationic, and amphoteric polymers, including acrylate-based polymers, polysaccharides, polyamino compounds, amphiphilic polymers, and other viscosity modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, cross-linked homopolymers of acrylic acid or of acrylamidopropane-sulfonic acid, associative polymers, non-associative thickening polymers, water-soluble thickening polymers, and mixtures of these.

Other suitable rheology modifiers or viscosity increasing agents include glycerol behenate, polyethylene and copolymers thereof such as PEG-150 distearate, magnesium stearate, synthetic polymers such as polyacrylic acid (available commercially as Carbomers) and acrylates copolymers such as sodium polyacrylate and polyacryloyldimethyl taurate, and mixtures of these.

The rheology modifier, or viscosity increasing agent, is present in the mascara formulation in an amount of from about 0.2 wt. % or greater, about 0.4 wt. % or greater, about 0.6 wt. % or greater, about 0.8 wt. % or greater, or about 1.0 wt. % or lower, about 1.2 wt. % or lower, about 1.4 wt. % or lower, about 1.6 wt. % or lower, or within any range using these endpoints.

4. Film Forming System

The mascara formulation includes a film forming system comprising a first film forming polymer and a second co-film former.

The first film forming polymer may be selected from acrylate copolymers, styrene/acrylate copolymers, acrylaminde/acrylate copolymers, polyurethanes, derivatives thereof and mixtures thereof. Acrylate copolymers may be chosen from copolymers comprising two or more monomers chosen from acrylic acid, methacrylic acid, and their simple esters, for example, lower alkyl esters such as methyl, ethyl, and ethylhexyl esters. Suitable acrylate copolymers may include ammonium acrylates copolymers, ethyl acrylates copolymers, acrylates/ethylhexylacrylate copolymers, acrylates/octylacrylates copolymers, alkyl (meth)acrylates copolymers, acrylates/$C_{12}$-$C_{22}$ alkylmethacrylate copolymers, ethylacrylate/methacrylic acid copolymer, and t-butyl acrylate/ethyl acrylate/methacrylic acid copolymer. Exemplary commercial acrylate copolymers include, but are not limited to, ALLIANZ™ OPT sold by Ashland Specialty Ingredients; COVACRYL A15 and COVACRYL E14 sold by Sensient Cosmetic Technologies LCW; DAITOSOL® 4000 SJT, DAITOSOL® 5000 AD, DAITOSOL® 5000 SJ, KOBOGUARD® 50A, and KOBOGUARD® 50N sold by Kobo Products, Inc.; DERMACRYL® AQF, YODOSOL 32A707, YODOSOL GH15, YODOSOL GH32, YODOSOL GH33, YODOSOL GH34, YODOSOL GH35, YODOSOL GH800, and YODOSOL GH810 sold by AkzoNobel; LUVIFLEX® SOFT, LUVIMER® 36D, and LUVIMER® 100P sold by BASF; and NEOCRYL® XK-90 sold by Neoresins, Inc.

The film forming agent may also be chosen from polyacrylates such as polyacrylate-21, and polyacrylate-15, and acrylates copolymer.

The film-forming agent may also be chosen from latex film forming polymers such as polyacrylate latex, polyurethrane latex, and their copolymers. Suitable examples of latex polymers may include ethylhexyl acrylate/hema copolymer (and) acrylates/diethylaminoethyl methacrylate/ethylhexyl acrylate copolymer (Syntran® PC 5775), styrene/acrylates/ammonium methacrylate copolymer (Syntran® 5760, Syntran® 5009, Syntran® PC5620), polyacrylate-21 (and) acrylates/dimethylaminoethyl methacrylate copolymer (Syntran® PC5100, Syntran® PC5776, Eudragit® E 100, Jurymer ET-410C), styrene/acrylates/ammonium methacrylate copolymer (Syntran® 5009 CG), olefin/acrylate grafted polymer (and) sodium laureth sulfate (and $C_{12}$-15 SEC-pareth 15 (Syntran® EX108), acrylates copolymer (Aculyn® 33A Polymer, Avalure® Ace 210/120/315 Acrylic Copolymer, Carbopol® Aqua SF-1 Polymer, Daitosol® 500 AD, Coatex® Co 633, Eliclear® 380/700/4U, Eudragit® L 100, Joncryl® 85, Luviflex® Soft), acrylates/ethylhexyl acrylate copolymer (Daitosol® 5000SJ, Daitosol® 4000SJT, MJA PS34-21, SDP-001). The Syntran® polymers are commercially available from the supplier Interpolymer Corp.

Suitable examples of latex polymers are polyurethane-35, polyurethane-35, and polyurethane-35.

The latex polymer may be an acrylate latex polymer, in particular styrene/acrylate copolymers. Suitable commercially available styrene/acrylate copolymers include, but are not limited to, DAITOSOL® 5000 STY sold by Kobo Products, Inc.; JONCRYL® 77 sold by BASF; NEOCRYL® BT-62 sold by Neoresins, Inc.; RHOPLEX™ P-376 and UCAR™ DL 432S sold by Dow Chemical Company; and YODOSOL GH41 and YODOSOL GH840 sold by AkzoNobel.

Acrylamide/acrylate copolymers may be chosen from acrylic acid/ethyl acrylate/t-butyl acrylamide copolymer, acrylates/octylacrylamide copolymer, and octylacrylamide/acrylates/methacrylates copolymer. Exemplary commercial acrylamide/acrylate copolymers include, but are not limited to, AMPHOMER® LV-71 and DERMACRYL® 79 sold by AkzoNobel and ULTRAHOLD® STRONG sold by BASF.

The co-film former may be a polymer such as divynyldimethicone/dimethicone copolymer, C12-13 pareth-23 and C12-13 pareth-3.

The film forming system is present in the mascara formulation in an amount of about 5 wt. % or greater, about 10 wt. % or greater, about 15 wt. % or greater, about 20 wt. % or greater, or about 25 wt. % or lower, about 30 wt. % or lower, about 35 wt. % or lower, about 40 wt. % or lower, or within any range using these endpoints.

The film forming system may include the first film forming polymer in an amount of about 7 wt. % or greater, about 10 wt. % or greater, about 15 wt. % or greater, or about 20 wt. % or less, about 25 wt. % or less, or within any range using these endpoints.

The film forming system may include the co-film former in an amount of about 0.2 wt. % or greater, about 0.5 wt. % or greater, about 1 wt. % or greater, or about 2 wt. % or less, about 3 wt. % or less, about 4 wt. % or less, about 5 wt. % or less, or within any range using these endpoints.

5. Water

The mascara formulation may include water in an amount of about 30 wt. % or greater, about 40 wt. % or greater, about 50 wt. % or greater, or about 60 wt. % or less, about 70 wt. % or less, or within any range using these endpoints.

6. Other Additives

The mascara formulation may include coalescents and/or plasticizers. It is known that inclusion of a coalescent agent promotes the coalescence of polymer particles in an aqueous dispersion, and inclusion of a plasticizer makes it possible to plasticize a polymer in an aqueous dispersion. Any coalescent and/or plasticizer may be used, and one of skill in the art will be able to choose an appropriate coalescent and/or plasticizer with little or no routine experimentation based on, for example, the type of cosmetic composition being formulated and the desired properties thereof.

Optional coalescents and/or plasticizers may be chosen from tributyl citrate, texanol ester alcohol, diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, and mixtures thereof. By way of example only, optional coalescents may be chosen from butylene glycol, caprylyl glycol, propylene glycol n-butyl ether, dipropylene glycol dibenzoate, dipropylene glycol dimethyl ether, propylene glycol methyl ether acetate, propylene glycol propyl ether, methyl lactate, ethyl lactate, isopropyl lactate, and mixtures thereof.

The coalescents and/or plasticizers may be present in the cosmetic composition in an amount of about 0.1 wt. % or greater, about 1 wt. % or greater, about 2 wt. % or greater, about 4 wt. % or greater, or about 6 wt. % or lower, about 8 wt. % or lower, about 10 wt. % or lower, or within any range using these endpoints.

The mascara formulation may also include one or more emollient/moisturizer. These compounds hydrate the lashes and also provide a "wet" texture and shiny look. Without limitation, useful emollients include, for example, carnauba wax, beeswax, mineral oil, almond oil, castor oil, sesame oil, hydrogenated polyisobutene, butylene glycol dicaprylte dicaprate (commercially available from Sasol as Myglyol®), and the like, and mixtures thereof. PEG-12 dimethicone as well as dimethicone/dimethicol may also be used as emollients.

The mascara formulation may include at least one pigment (or dyestuff). Suitable pigments/dyes include, but are not limited to, pulverulent dyestuffs, liposoluble dyes, and water-soluble dyes.

The pulverulent dyestuffs may, for instance, be chosen from pigments and nacres. Suitable pigments include titanium dioxide, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

The nacres which may be used include, for example, colored nacreous pigments such as titanium mica with iron oxides, titanium mica with ferric blue or chromium oxide, titanium mica with an organic pigment chosen from those listed above, and nacreous pigments based on bismuth oxychloride.

The at least one pigment/dyestuff may be present in the mascara formulation in an amount ranging from about 1 wt. % or greater, about 5 wt. % or greater, about 10 wt. % or greater, about 15 wt. % or greater, about 20 wt. % or greater, or about 25 wt. % or lower, about 30 wt. % or lower, about 35 wt. % or lower, about 40 wt. % or lower, or within any range using these endpoints.

The mascara formulation may further include fillers, fibers, solvents, dispersants, antioxidants, preservatives, fragrances, additional thickeners or texturizers, liquid lipids/oils, additional viscosity modifiers, additional film formers, sunscreen agents, additional pigments/colorants/dyes, silica, clays, humectants and moisturizing agents, emulsifying agents, additional structuring agents and fillers, surfactants, shine agents, conditioning agents, cosmetically, dermatologically and pharmaceutically active agents, vitamins, plant extracts, additional film-formers, coalescents/plasticizers, pH modifiers/neutralizing agents, stabilizers, and mixtures thereof.

V. Toothpastes

The present disclosure further provides formulations of toothpastes. The toothpaste formulations may be used to improve oral health, remove stains, and prevent caries.

The toothpaste formulation may include a basic amino acid in free or salt form, calcium carbonate, a fluoride ion source, a flavoring agent, one or more surfactants chosen from one or more surfactant classes, water, and other optional additives.

1. Amino Acids

The toothpaste formulation may include a basic amino acid in free or salt form. Suitable amino acids include not only naturally occurring basic amino acids such as arginine, lysine and histidine, but also any basic amino acids having a carboxyl group and an amino group in the molecule which are water-soluble and provide an aqueous solution with a pH of about 7 or greater. For example, basic amino acids may include but are not limited to arginine, lysine, citrulline, ornithine, creatine, histidine, diaminobutanoic acid, diamine propionic acid, salts thereof and combinations thereof. In certain embodiments the basic amino acid may comprise arginine, citrulline, ornithine and salts and combinations thereof.

The basic amino acid may be in free or salt form. In the case of salts, such salts should be pharmaceutically acceptable. The basic amino acid may be a salt derived from a pharmaceutically acceptable inorganic or organic acid or base, for example an acid addition salt formed by an acid which forms a physiologically acceptable anion, for example hydrochloride or bromide, or a base addition salt formed by a base which forms a physiologically acceptable cation such as an alkali metal or alkaline earth metal, for example potassium, sodium, calcium or magnesium. The basic amino acid may be a bicarbonate salt of an amino acid.

The basic amino acid in free or salt form is present in an amount from 0.5 wt. % or greater, about 1 wt. % or greater, about 2 wt. % or greater, or about 3 wt. % or lower, about 4 wt. % or lower, about 5 wt. % or lower, or within any range using these endpoints.

2. Calcium Carbonate

The toothpaste formulation may include calcium carbonate. Natural calcium carbonate is found in rocks such as chalk, limestone, marble and travertine, as well as egg shells and mollusk shells. Natural calcium carbonate can be used as an abrasive in oral care compositions. Typically, natural calcium carbonate abrasive is finely ground limestone which may optionally be refined or partially refined to remove impurities. In certain embodiments, the natural calcium carbonate has an average particle size of less than 10 microns, for example 3 to 7 microns or about 5.5 microns.

The toothpaste formulation may include additional calcium-containing abrasives, for example a calcium phosphate abrasive such as tricalcium phosphate, hydroxyapatite or dicalcium phosphate dehydrate. In certain embodiments the composition comprises silica abrasives such as precipitated silicas having a mean particle size of up to about 20 μm, sodium metaphosphate, potassium metaphosphate, aluminium silicate, calcined alumina, bentonite or other siliceous materials and/or combinations thereof.

The amount of calcium carbonate in the toothpaste formulation may be about 20 wt. % or greater, about 25 wt. % or greater, about 30 wt. % or greater, about 35 wt. % or greater, or about 40 wt. % or lower, about 45 wt. % or lower, about 50 wt. % or lower, about 55 wt. % or lower, about 60 wt. % or lower, or within any range using these endpoints.

3. Fluoride Ion Source

The composition may include one or more fluoride ion sources, such as soluble fluoride salts. Suitable fluoride ion sources include stannous fluoride, sodium fluoride, potassium fluoride, sodium monofluorophosphate, sodium fluorosilicate, ammonium, fluorosilicate, amine fluoride, ammonium fluoride and combinations of one or more thereof.

The fluoride ion source may be present in an amount sufficient to supply about 25 ppm to about 25,000 ppm fluoride ions, for example from about 500 ppm to about 200 ppm, from about 1000 ppm to about 1600 ppm.

The weight of fluoride salt may be selected in order to provide the appropriate level of fluoride ion in the toothpaste formulation. The fluoride salt may be present in an amount of about 0.01 wt. % or greater, about 1 wt. % or greater, about 2 wt. % or greater, about 4 wt. % or greater, or about 6 wt. % or lower, about 8 wt. % or lower, about 10 wt. % or lower, or within any range using these endpoints.

4. Surfactant

The toothpaste formulation includes one or more surfactants chosen from one or more surfactant classes. The surfactants function as stabilizers for the toothpaste formulation.

Suitable surfactants for use in the toothpaste formulations of the present disclosure include one or more surfactants and/or co-surfactants of Formula I,

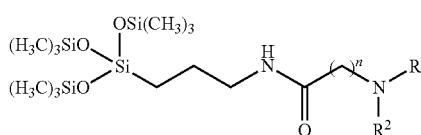

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The one or more surfactants are present in the toothpaste formulation in an amount of about 1.0 wt. % or greater, about 1.1 wt. % or greater, about 1.2 wt. % or greater, about 1.3 wt. % or less, about 1.4 wt. % or less, or within any range using these endpoints.

5. Flavoring Agent

The toothpaste formulation may include a flavoring agent. The flavoring agent may comprise one or more essential oils as well as various flavoring aldehydes, esters and/or alcohols. Suitable flavoring agents may include one or more essential oil selected from oils of peppermint, wintergreen, sassafras, clove, sage, eucalyptus, marjoram, cinnamon, lemon, lime, grapefruit and orange.

The flavoring agent may be present in the composition in an amount of about 0.1 wt. % or greater, about 1.2 wt. % or greater, about 1.4 wt. % or greater, or about 1.6 wt. % or lower, about 1.8 wt. % or lower, about 2.0 wt. % or lower, or within any range using these endpoints.

6. Other Additives

The toothpaste formulation may include other additives, such as a bacteriostatic preservative such as benzyl alcohol.

Benzyl alcohol may be present in the toothpaste formulation in an amount of about 0.2 wt. % or greater, about 0.3 wt. % or greater, about 0.4 wt. % or greater, about 0.5 wt. % or greater, or about 0.6 wt. % or lower, about 0.7 wt. % or lower, about 0.8 wt. % or lower, or within any range using these endpoints.

The toothpaste formulation may also include one or more polymers, such as polyethylene glycols, polyvinylmethyl ether maleic acid copolymers and polysaccharides (e.g. cellulose derivatives such as carboxymethyl cellulose or microcrystalline cellulose, or polysaccharide gums such as xanthan gum or carrageenan gum). Acidic polymers, for example polyacrylate gels, may be provided as free acids or partially or fully neutralized water-soluble alkali metal (e.g. potassium and sodium) or ammonium salts.

The toothpaste formulation may also include one or more humectants. Humectants can prevent the composition from hardening upon exposure to air. In certain embodiments the composition comprises one or more humectants selected from edible polyhydric alcohols such as glycerine, sorbitol, xylitol, propylene glycol and mixtures thereof.

7. Method of Making

The present disclosure further provides a method of preparing a formulation for use as a toothpaste. The method may comprise the sequential steps of: a) adding the basic amino acid to a solution comprising the fluoride ion source, b) adding the calcium carbonate, and c) adding the anionic surfactant.

VI. Surfactants

The present disclosure provides surfactants for use in personal care products in the form of siloxane derivatives of amino acids. The amino acids may be naturally occurring or synthetic, or they may be obtained from ring-opening reactions of lactams, such as caprolactam. The compounds of the present disclosure have been shown to have surface-active properties, and may be used as surfactants and wetting agents, for example. In particular, the present disclosure provides compounds of Formula I, shown below:

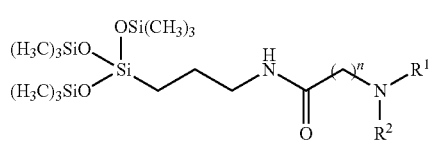

Formula I wherein $R^1$ and $R^2$ may be the same or different, and are at least one group selected from the group consisting of $C_1$-$C_6$ alkyl, optionally the $C_1$-$C_6$ alkyl may include one or more of oxygen, nitrogen, or sulfur atoms or substituents that include one or more of these atoms, the alkyl chain may be optionally substituted with one or more substituents selected from the group consisting of hydroxyl, amino, amido, sulfonyl, sulfonate, carbonyl, carboxyl, and carboxylate;

n is an integer from 1 to 12;

the terminal nitrogen is optionally further substituted with $R^3$, wherein $R^3$ is selected from the group consisting of hydrogen, oxygen, hydroxyl, and $C_1$-$C_6$ alkyl; and an optional counterion may be associated with the compound and, if present, the counterion may be selected from the group consisting of chloride, bromide, and iodide.

The present disclosure further provides for compounds of Formula Ia:

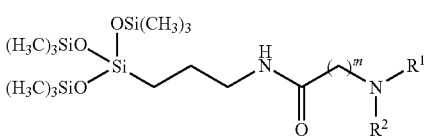

Formula Ia wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;

m is an integer from 1 to 6;

the terminal nitrogen is optionally further substituted with $R^3$, wherein $R^3$ is selected from the group consisting of hydrogen, oxygen, and $C_1$-$C_6$ alkyl wherein the alkyl chain is optionally substituted with one or more substituents selected from the group consisting of carboxyl, carboxylate, and sulfonate; and an optional counterion may be associated with the compound and, if present, the counterion may be selected from the group consisting of chloride, bromide, and iodide.

The present disclosure additionally provides for compounds of Formula Ib:

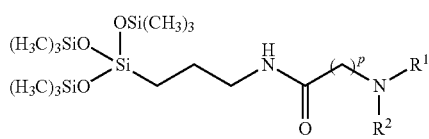

Formula Ib wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;

p is 5;

the terminal nitrogen is optionally further substituted with $R^3$, wherein $R^3$ is selected from the group consisting of hydrogen, oxygen, and $C_1$-$C_6$ alkyl, wherein the alkyl chain is optionally substituted with one or more substituents selected from the group consisting of carboxyl, carboxylate, and sulfonate; and an optional counterion may be associated with the compound and, if present, the counterion may be selected from the group consisting of chloride, bromide, and iodide.

One specific compound provided by the present disclosure is 6-(dimethylamino)-N-(3-(1,1,1,5,5,5-hexamethyl-3-((trimethylsilyl)oxy)trisiloxan-3-yl)propyl)hexanamide (Surfactant 1), having the following formula:

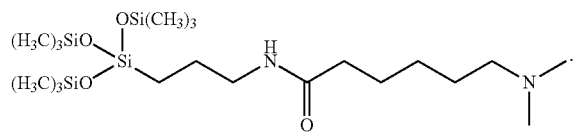

A second specific compound provided by the present disclosure is 6-(dimethylamino)-N-(3-(1,1,1,5,5,5-hexamethyl-3-((trimethylsilyl)oxy)trisiloxan-3-yl)propyl)hexaminium chloride (Surfactant 2), having the following formula:

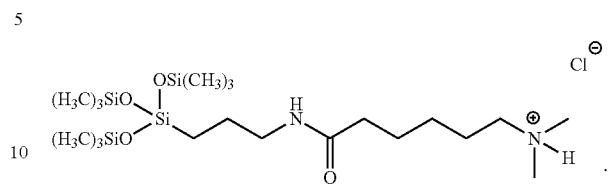

A third specific compound provided by the present disclosure is 3 6-((3-(1,1,1,5,5,5-hexamethyl-3-((trimethylsilypoxy)trisiloxan-3-yl)propyl)amino)-N,N,N-trimethyl-6-oxohexan-1-aminium iodide (Surfactant 3), having the following formula:

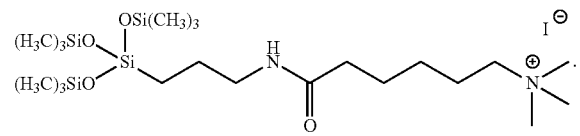

A fourth specific compound provided by the present disclosure is 6-((3-(1,1,1,5,5,5-hexamethyl-3-((trimethylsilypoxy)trisiloxan-3-yl)propyl)amino)-N,N-dimethyl-6-oxohexan-1-amine oxide (Surfactant 4), having the following formula:

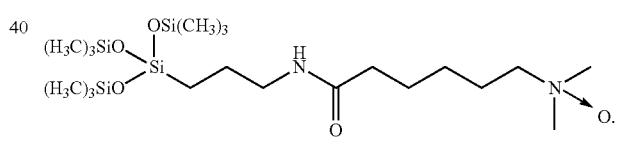

In the structure above, the notation "NO" is intended to convey a non-ionic bonding interaction between nitrogen and oxygen.

A fifth specific compound provided by the present disclosure is 4-((6-((3-(1,1,1,5,5,5-hexamethyl-3-((trimethylsilypoxy)trisiloxan-3-yl)propyl)amino)-6-oxohexyl)dimethylammonio)butane-1-sulfonate (Surfactant 5), having the following formula:

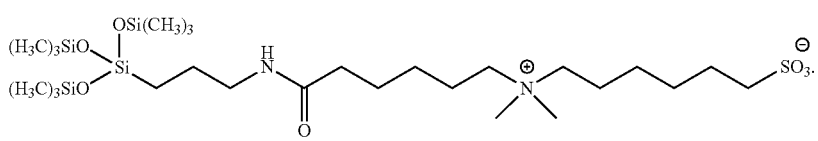

A sixth specific compound provided by the present disclosure is 5-((6-((3-(1,1,1,5,5,5-hexamethyl-3-((trimethylsilyl)oxy)trisiloxan-3-yl)propyl)amino)-6-oxohexyl)dimethylammonio)pentane-1-sulfonate (Surfactant 6), having the following formula:

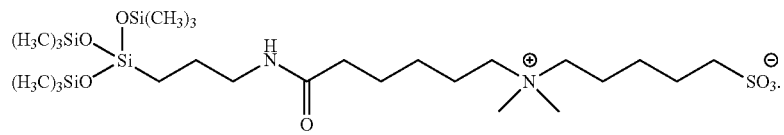

These compounds may be synthesized by various methods. One such method includes reacting an amino acid, such as an N-alkylated or N-acylated amino acid, with a siloxane to convert the amino acid C-terminus to the desired siloxane derivative. The amino acid N-terminus may be further protonated, alkylated, or oxidized to yield a quaternary amine or an N-oxide, for example.

The amino acid may be naturally occurring or synthetic or may be derived from a ring opening reaction of a lactam, such as caprolactam. The ring-opening reaction may be either an acid or alkali catalyzed reaction, and an example of an acid catalyzed reaction is shown below in Scheme 1.

SCHEME 1

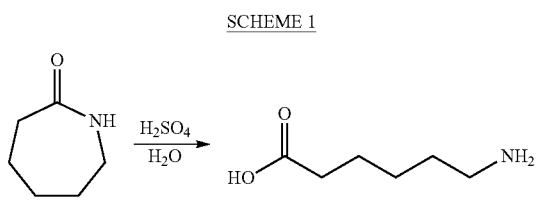

The amino acid may have as few as 1 or as many as 12 carbons between the N- and C-terminii. The alkyl chain may be branched or straight. The alkyl chain may be interrupted with nitrogen, oxygen, or sulfur. The alkyl chain may be further substituted with one or more substituents selected from the group consisting of hydroxyl, amino, amido, sulfonyl, sulfonate, carboxyl, and carboxylate. The N-terminal nitrogen may be acylated or alkylated with one or more alkyl groups. For example, the amino acid may be 6-(dimethylamino)hexanoic acid.

The siloxane may be substituted with one or more alkoxy groups, such as methoxy, ethoxy, isopropoxy, tertiary butoxy, and others. The siloxane may be further substituted with one or more alkyl groups, such as propyl, wherein the alkyl group may yet be further substituted with an appropriate functional group to permit coupling of the siloxane to the amino acid, such as a nitrogen. For example, the siloxane may be 3-aminopropyltris(trimethylsiloxy)silane.

The siloxane derivative of the amino acid may be synthesized as shown below in Scheme 2. As shown, 6-aminohexanoic acid is treated with formaldehyde in formic acid at reflux to give 6-(dimethylamino)hexanoic acid. The free carboxylic acid is then coupled to 3-aminopropyl(trimethylsiloxy)silane in refluxing toluene to give the desired siloxane derivative.

SCHEME 2

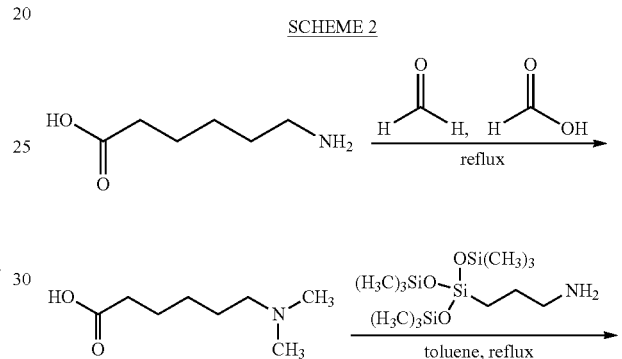

The N-terminal nitrogen may be further derivatized to modify or improve water solubility and surface-active properties. A sample synthetic scheme is shown below in Scheme 3, in which the N-terminal nitrogen is treated with hydrochloric acid to give the corresponding hydrochloride salt.

SCHEME 3

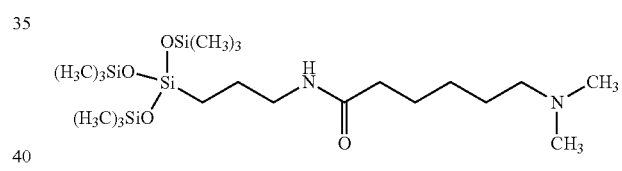

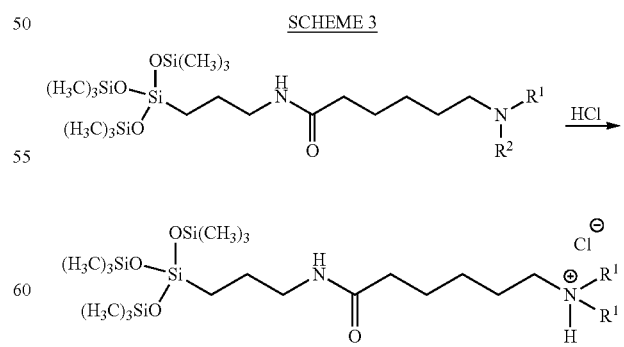

The N-terminal nitrogen may be alkylated. A sample synthetic scheme is shown below, in which the N-terminal nitrogen is treated with methyl iodide to give the corresponding quaternary amine salt.

SCHEME 4

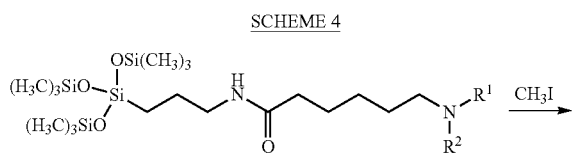

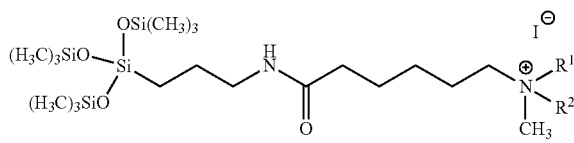

The N-terminal nitrogen may be treated with hydrogen peroxide in water at reflux to give the corresponding N-oxide, as shown in the sample synthetic scheme below, Scheme 5.

SCHEME 5

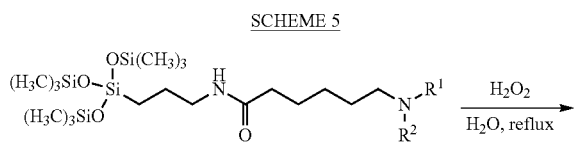

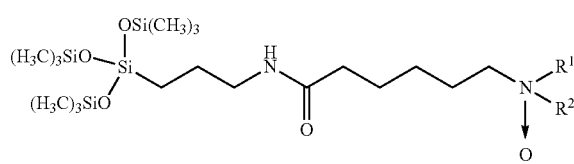

The compounds of the present disclosure demonstrate surface-active properties. These properties may be measured and described by various methods. One method by which surfactants may be described is by the molecule's critical micelle concentration (CMC). CMC may be defined as the concentration of a surfactant at which micelles form, and above which all additional surfactant is incorporated into micelles.

As surfactant concentration increases, surface tension decreases. Once the surface is completely overlaid with surfactant molecules, micelles begin to form. This point represents the CMC, as well as the minimum surface tension. Further addition of surfactant will not further affect the surface tension. CMC may therefore be measured by observing the change in surface tension as a function of surfactant concentration. One such method for measuring this value is the Wilhemy plate method. A Wilhelmy plate is usually a thin iridium-platinum plate attached to a balance by a wire and placed perpendicularly to the air-liquid interface. The balance is used to measure the force exerted on the plate by wetting. This value is then used to calculate the surface tension ($\gamma$) according to Equation 1:

$$\gamma = F/l \cos \theta \quad \text{Equation 1:}$$

wherein l is equal to the wetted perimeter (2w+2d, in which w and d are the plate thickness and width, respectively) and cos θ, the contact angle between the liquid and the plate, is assumed to be 0 in the absence of an extant literature value.

Another parameter used to assess the performance of surfactants is dynamic surface tension. The dynamic surface tension is the value of the surface tension for a particular surface or interface age. In the case of liquids with added surfactants, this can differ from the equilibrium value. Immediately after a surface is produced, the surface tension is equal to that of the pure liquid. As described above, surfactants reduce surface tension; therefore, the surface tension drops until an equilibrium value is reached. The time required for equilibrium to be reached depends on the diffusion rate and the adsorption rate of the surfactant.

One method by which dynamic surface tension is measured relies upon a bubble pressure tensiometer. This device measures the maximum internal pressure of a gas bubble that is formed in a liquid by means of a capillary. The measured value corresponds to the surface tension at a certain surface age, the time from the start of the bubble formation to the occurrence of the pressure maximum. The dependence of surface tension on surface age can be measured by varying the speed at which bubbles are produced.

Surface-active compounds may also be assessed by their wetting ability on solid substrates as measured by the contact angle. When a liquid droplet comes in contact with a solid surface in a third medium, such as air, a three-phase line forms among the liquid, the gas and the solid. The angle between the surface tension unit vector, acting at the three-phase line and tangent at the liquid droplet, and the surface is described as the contact angle. The contact angle (also known as wetting angle) is a measure of the wettability of a solid by a liquid. In the case of complete wetting, the liquid is completely spread over the solid and the contact angle is 0°. Wetting properties are typically measured for a given compound at the concentration of 1-100×CMC, however, it is not a property that is concentration-dependent therefore measurements of wetting properties can be measured at concentrations that are higher or lower.

In one method, an optical contact angle goniometer may be used to measure the contact angle. This device uses a digital camera and software to extract the contact angle by analyze the contour shape of a sessile droplet of liquid on a surface.

Potential applications for the surface-active compounds of the present disclosure include formulations for use as shampoos, hair conditioners, detergents, spot-free rinsing solutions, floor and carpet cleaners, cleaning agents for graffiti removal, wetting agents for crop protection, adjuvants for crop protection, and wetting agents for aerosol spray coatings.

It will be understood by one skilled in the art that small differences between compounds may lead to substantially different surfactant properties, such that different compounds may be used with different substrates, in different applications.

The following non-limiting embodiments are provided to demonstrate the different properties of the different surfactants. In Table 1 below, short names for the surfactants are correlated with their corresponding chemical structures.

TABLE 1

| Surfactant | Formula & Name |
|---|---|
| Surfactant 1 | 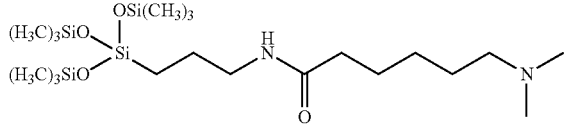  6-(dimethylamino)-N-(3-(1,1,1,5,5,5-hexamethyl-3-((trimethylsilyl)oxy)trisiloxan-3-yl)propyl)hexanamide |
| Surfactant 2 | 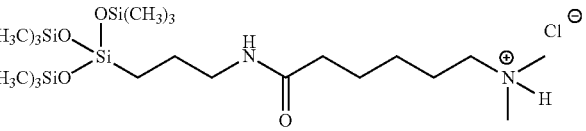  6-((3-(1,1,1,5,5,5-hexamethyl-3-((trimethylsilyl)oxy)trisiloxan-3-yl)propyl)amino)-N,N-dimethyl-6-oxohexan-1-aminium chloride |
| Surfactant 3 | 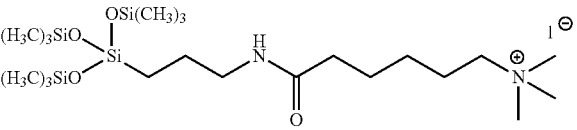  6-((3-(1,1,1,5,5,5-hexamethyl-3-((trimethylsilyl)oxy)trisiloxan-3-yl)propyl)amino)-N,N,N-trimethyl-6-oxohexan-1-aminium iodide |
| Surfactant 4 | 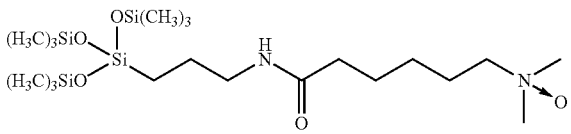  6-((3-(1,1,1,5,5,5-hexamethyl-3-((trimethylsilyl)oxy)trisiloxan-3-yl)propyl)amino)-N,N-dimethyl-6-oxohexan-1-amine oxide |
| Surfactant 5 | 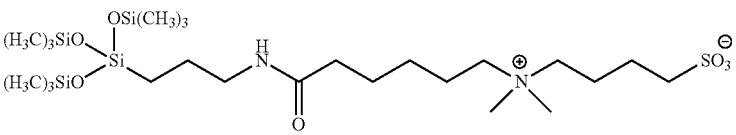  4-((6-((3-(1,1,1,5,5,5-hexamethyl-3-((trimethylsilyl)oxy)trisiloxan-3-yl)propyl)amino)-6-oxohexyl)dimethylammonio)butane-1-sulfonate |

Each of the five compounds are effective as surface-active agents, useful for wetting or foaming agents, dispersants, emulsifiers, and detergents, among other applications.

Surfactants 1 and 2 candidates for use in a variety of surface cleaning and personal care product formulations as foaming or wetting agents.

Surfactant 3 is cationic. These surfactants are useful in both the applications described above and some further special applications such as surface treatments, such as in personal hair care products, and can also be used to generate water repellant surfaces.

Surfactant 4 is non-ionic, and can be used in shampoos, detergents, hard surface cleaners, and a variety of other surface cleaning formulations.

Surfactant 5 is zwitterionic. These surfactants are useful as co-surfactants in all of the applications described above.

The amount of the compounds disclosed herein used in a formulation may be as low as about 0.001 wt. %, about 0.05 wt. %, about 0.1 wt. %, about 0.5 wt. %, about 1 wt. %, about 2 wt. %, or about 5 wt. %, or as high as about 8 wt. %, about 10 wt. %, about 15 wt. %, about 20 wt. %, or about 25 wt. %, or within any range using any two of the foregoing values.

EXAMPLES

Nuclear magnetic resonance (NMR) spectroscopy was performed on a Bruker 500 MHz spectrometer. The critical micelle concentration (CMC) was determined by the Wilhelmy plate method at 23° C. with a tensiometer (DCAT 11, DataPhysics Instruments GmbH) equipped with a Pt—Ir plate. Dynamic surface tension was determined with a bubble pressure tensiometer (Krüss BP100, Krüss GmbH), at 23° C. Contact angle was determined with the optical contact angle goniometer (OCA 15 Pro, DataPhysics GmbH) equipped with a digital camera.

Example 1a

Synthesis of 6-(dimethylamino)-N-(3-(1,1,1,5,5,5-hexamethyl-3-((trimethylsilyl)oxy)trisiloxan-3-yl)propyl)hexanamide (Surfactant 1) and 6-((3-(1,1,1,5,5,5-hexamethyl-3-((trimethylsilypoxy)trisiloxan-3-yl)propyl)amino)-N,N-dimethyl-6-oxohexan-1-aminium salt (Surfactant 2)

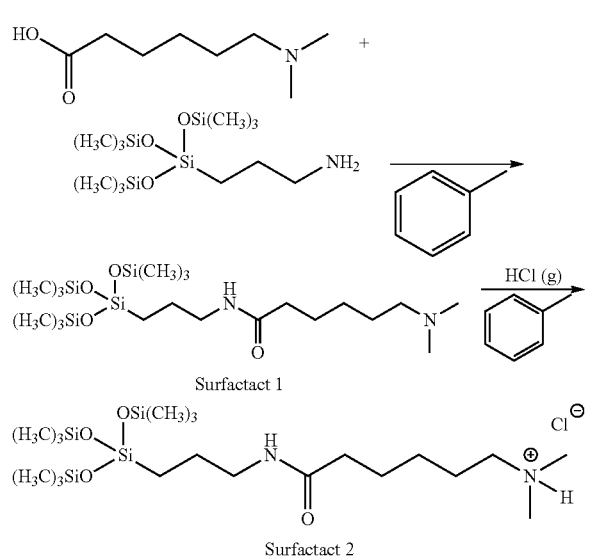

6-(Dimethylamino)hexanoic acid (2.00 g, 12.56 mmol, 1 equiv.) was dissolved in toluene (50 mL) in a 100 mL round bottom boiling flask equipped with a Dean Stark trap, then 3-aminopropyltris(trimethylsiloxy)silane (5.48 mL, 13.81 mmol, 1.1 equiv.) was added. The reaction vessel was heated, and the reaction refluxed for 24 hours until no more water separated in the Dean Stark tube. The solvent was removed under vacuum to give Surfactant 1 as a yellow oil in 94% yield. $^1$H NMR (500 MHz, DMSO) δ: 0.09 (s, 27H), 0.28-0.31 (m, 2H), 1.12-1.26 (m, 2H), 1.27-1.30 (m, 4H), 1.38-1.41 (m, 2H), 1.94 (t, J=7.3 Hz, 2H), 2.00 (s, 6H), 2.06-2.03 (m, 2H), 2.89 (dd, J=12.9, 6.8 Hz, 2H).

In its neutral form, Surfactant 1 is slightly soluble in pure water without addition of hydrotropes or other surfactants, but after protonation in slightly acidic conditions it becomes interfacially active (Surfactant 2). The acidic conditions can be generated by the addition of any acid or acidic buffer in the pH range of 4-7. Surfactant 2 can also be prepared in non-aqueous solutions, for example by sparging gaseous HCl in toluene in the presence of Surfactant 1.

Example 1b

Determination of Critical Micelle Concentration (CMC) of Surfactant 2

The critical micelle concentration (CMC) for Surfactant 2 was tested with a chloride counterion and was determined to be about 2 mmol. The plateau value of minimum surface tension that can be reached by this surfactant is about 23 mN/m. FIG. 1 is a plot of these results, showing surface tension versus concentration.

Example 2a

Synthesis of 6-((3-(1,1,1,5,5,5-hexamethyl-3-((trimethylsilyl)oxy)trisiloxan-3-yl)propyl)amino)-N,N,N-trimethyl-6-oxohexan-1-aminium iodide (Surfactant 3)

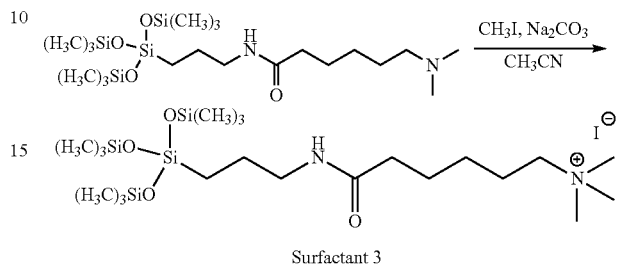

Surfactant 1 (1.00 g, 2.02 mmol, 1 equiv.) was dissolved in acetonitrile (10 mL) in a 100 mL round bottom flask. Next, Na$_2$CO$_3$ (0.26 g, 2.42 mmol, 1.2 equiv.) was added and the mixture was stirred for 10 minutes. Methyl iodide (0.377 mL, 6.06 mmol, 3 equiv.) was added and the reaction was heated at 40° C. for 24 hours. The cooled reaction mixture was filtered, and the solvent was removed under vacuum to give Surfactant 3 as a slightly yellow solid in quantitative yield. $^1$H NMR (500 MHz, DMSO) δ 0.09 (s, 27H), 0.38-0.42 (m, 2H), 1.23-1.26 (m, 2H), 1.37-1.40 (m, 2H), 1.52-1.55 (m, 2H), 1.65-1.69 (m, 2H), 2.08 (t, J=7.4 Hz, 2H), 2.99 (dd, J=13, 6.9 Hz, 2H), 3.04 (s, 9H), 3.24-3.33 (m, 2H).

The pure product is soluble in water and has surfactant properties. The halogen anions may be directly obtained from the N-alkylation reaction, and other desired counter anions may be obtained by anion exchange.

Example 2b

Determination of Physical Properties of Surfactant 3

Figure 2:
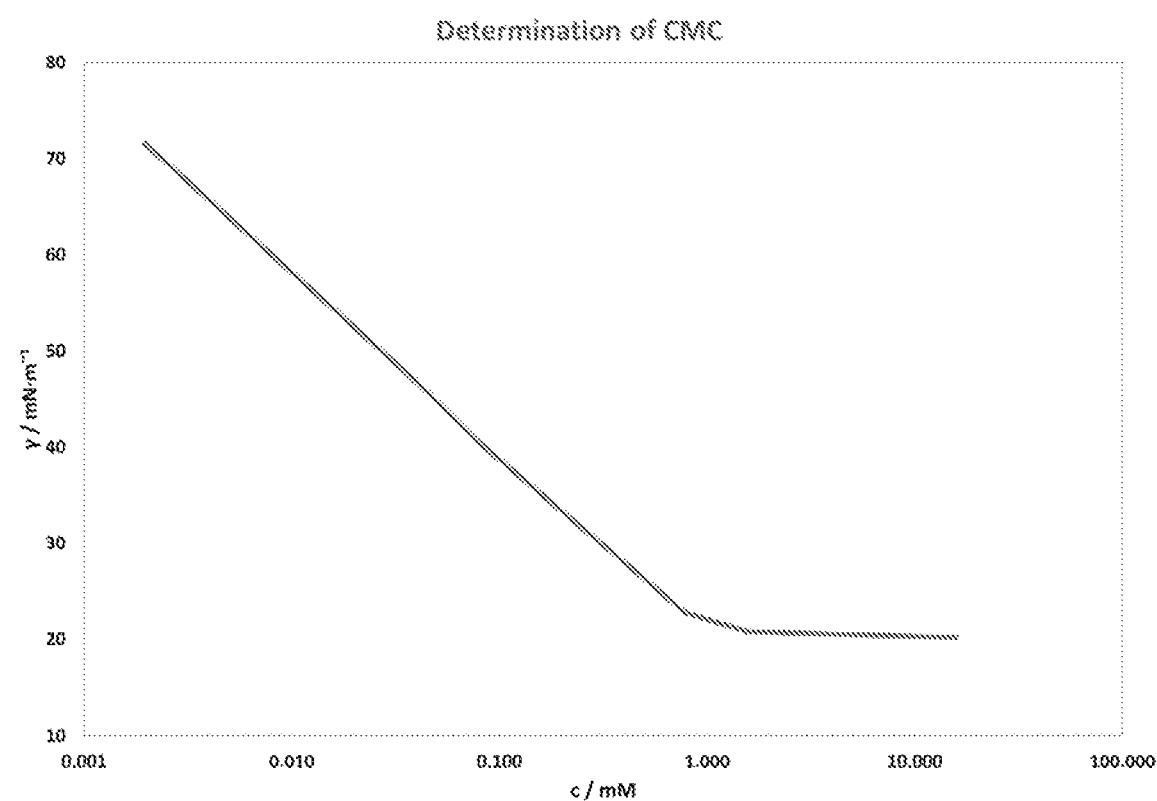
FIG. 2 shows a plot of surface tension versus concentration for Surfactant 3 as described in Example 2b.

The critical micelle concentration (CMC) for Surfactant 3 was measured. From the surface tension change with concentration in water, the CMC was determined to be about 1.6 mmol. The plateau value of minimum surface tension that can be reached by this surfactant is around 20 mN/m, indicating that the surfactant has outstanding interfacial activity. These results are plotted as surface tension versus concentration in FIG. 2.

Figure 3:
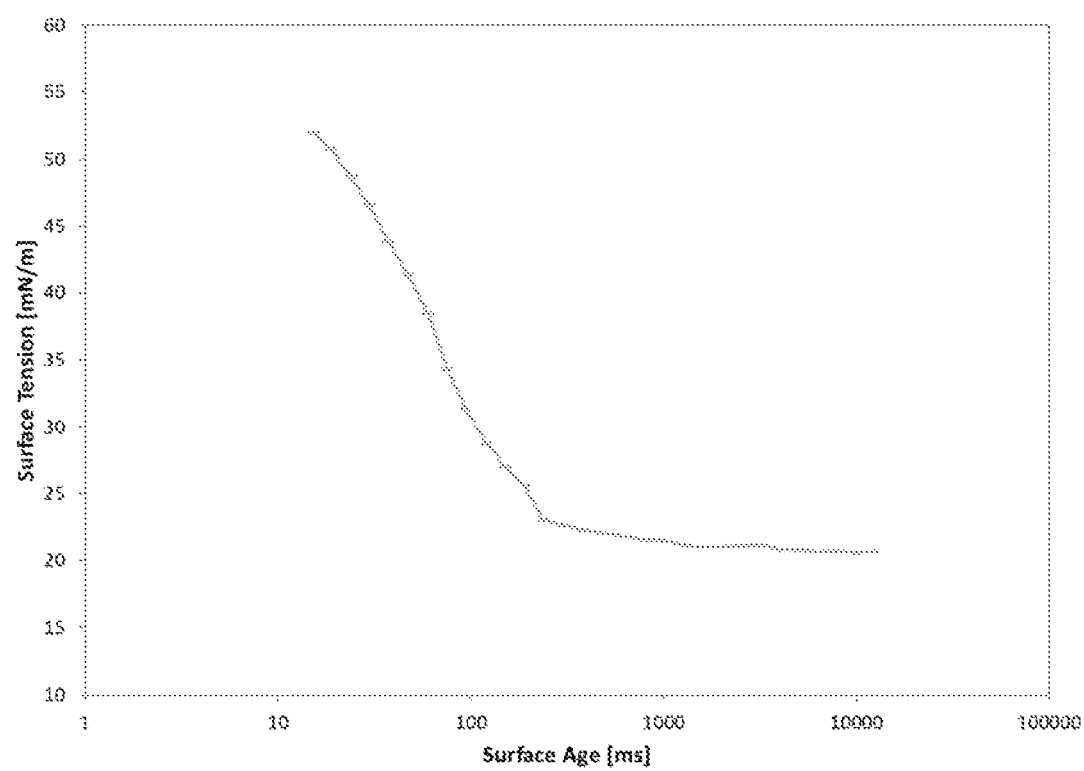
FIG. 3 shows a plot of dynamic surface tension as change in surface tension versus time for Surfactant 3 as described in Example 2b.

The dynamic surface tension of Surfactant 3 was determined with a bubble pressure tensiometer which measures the change of surface tension of a freshly created air-water interface with time. FIG. 3 shows a plot of the results as surface tension versus time and demonstrates that Surfactant 3 fully saturated the interface in less than 500 ms, making it exceptionally fast in terms of interfacial adsorption.

In addition to Surfactant 3's ability to lower both interfacial and surface tension, formulations containing only Surfactant have exceptional wetting properties. For example, hydrophobic substrates such as polyethylene and polypropylene exhibit a total surface wetting with a contact angle of 0°. On oleophobic and hydrophobic substrates such as Teflon, the measured contact angle was extremely low, 10.5° (Table 2).

TABLE 2

| Substrate | CA of Surfactant 3 (°) | Concentration | CA of water (°) |
|---|---|---|---|
| Teflon | 10.5 | 10x CMC | 119 |
| Polyethylene | 0 | 10x CMC | 91.5 |
| Polypropylene | 0 | 10x CMC | 93.3 |
| Nylon | 0 | 10x CMC | 50 |
| Polyethylene terephthalate | 0 | 10x CMC | 65.3 |

Example 3a

Synthesis of 6-((3-(1,1,1,5,5,5-hexamethyl-3-((trimethylsilyl)oxy)trisiloxan-3-yl)propyl)amino)-N,N-dimethyl-6-oxohexan-1-amine oxide (Surfactant 4)

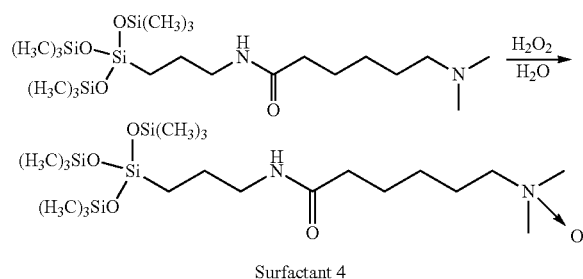

Surfactant 4

Surfactant 1 (1.00 g, 2.02 mmol, 1 equiv.) was added to distilled water (80 mL) in a 100 mL round bottom flask, followed by 50% hydrogen peroxide (1.15 mL, 20.2 mmol, 10 equiv.). The reaction was refluxed for 12 hours, then concentrated under vacuum. The residue was washed three times with acetone to give Surfactant 4 in 99% yield. $^1$H NMR (500 MHz, DMSO) δ 0.09 (s, 27H), 0.38-0.44 (m, 2H), 1.21-1.25 (m, 2H), 1.35-1.42 (m, 2H), 1.50-1.55 (m, 2H), 1.71-1.75 (m, 2H), 2.05-2.08 (m, 2H), 2.97-3.00 (m, 2H), 3.01 (s, 9H), 3.11-3.14 (m, 2H).

Example 3b

Determination of Physical Properties of Surfactant 4

Figure 4:
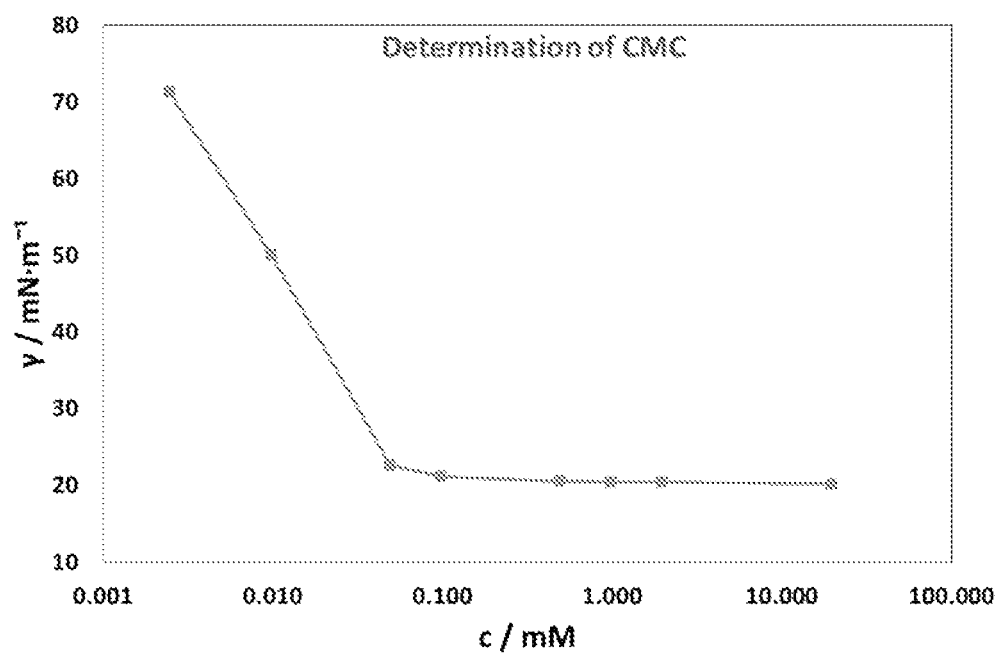
FIG. 4 shows a plot of surface tension versus concentration for Surfactant 4 as described in Example 3b.

The critical micelle concentration (CMC) for Surfactant 4 was measured. From the surface tension change with concentration in water, the CMC was determined to be about 0.49 mmol. The plateau value of minimum surface tension that can be reached by this surfactant is about 20 mN/m, indicating that the surfactant has outstanding interfacial activity. These results are plotted as surface tension versus concentration in FIG. 4.

Figure 5:
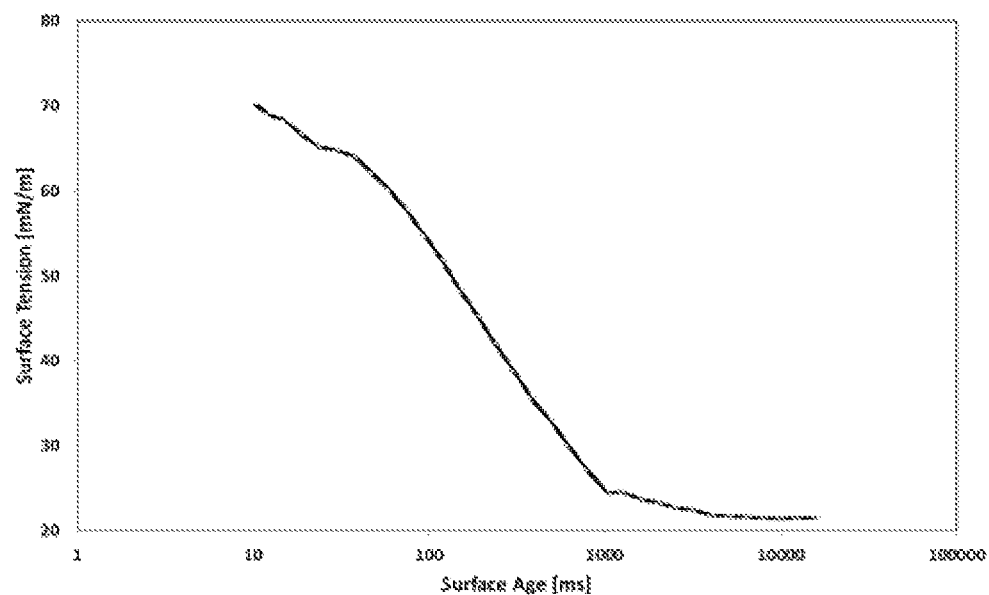
FIG. 5 shows a plot of dynamic surface tension as change in surface tension versus time for Surfactant 4 as described in Example 3b.

The dynamic surface tension of Surfactant 4 was determined with a bubble pressure tensiometer. FIG. 5 shows a plot of the results as surface tension versus time and demonstrates that Surfactant 4 fully saturated a freshly created air-water interface in one second or less, making it fast in terms of interfacial adsorption.

In addition to Surfactant 4's ability to lower both the interfacial and surface tension, formulations containing only Surfactant 4 in concentrations of 1-100×CMC have exceptional wetting properties. For example, a solution of Surfactant 4 in water at a concentration of 10×CMC exhibits a 0° contact angle on hydrophobic substrates such as polyethylene and polypropylene, and 10.6° on oleophobic and hydrophobic substrates such as Teflon. These contact angles are extremely low in comparison with the contact angle of water on the same substrate (Table 3).

TABLE 3

| Substrate | CA of Surfactant 4 (°) | Concentration | CA of water (°) |
|---|---|---|---|
| Teflon | 10.6 | 10x CMC | 119 |
| Polyethylene | 0 | 10x CMC | 91.5 |
| Polypropylene | 0 | 10x CMC | 93.3 |
| Nylon | 0 | 10x CMC | 50 |
| Polyethylene terephthalate | 0 | 10x CMC | 65.3 |

Example 4a

Synthesis of 4-((6-((3-(1,1,1,5,5,5-hexamethyl-3-((trimethylsilyl)oxy)trisiloxan-3-yl)propyl)amino)-6-oxohexyl)dimethylammonio)butane-1-sulfonate (Surfactant 5)

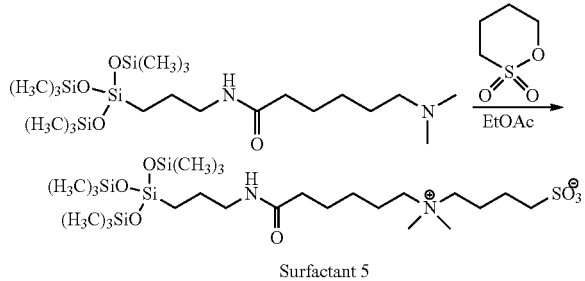

Surfactant 5

Surfactant 1 (1.00 g, 2.02 mmol, 1 equiv.) was added to ethyl acetate (EtOAc) (30 mL) in a 100 mL round bottom flask, followed by 1,2-butane sultone (0.27 mL, 2.2 mmol, 1.1 equiv.). The reaction was refluxed for 12 hours, after which the solvent was removed and the resultant white waxy solid was washed with acetone to give Surfactant 5 in 50% yield. $^1$H NMR (500 MHz, DMSO) δ 0.10 (s, 27H), 0.38-0.46 (m, 2H), 1.23-1.27 (m, 2H), 1.37-1.68 (m, 10H), 1.73-1.78 (m, 2H), 2.45-2.48 (m, 2H), 2.97-3.01 (m, 8H), 3.18-3.21 (m, 2H), 3.23-3.27 (m, 2H).

Example 4b

Determination of Physical Properties of Surfactant 5

Figure 6:
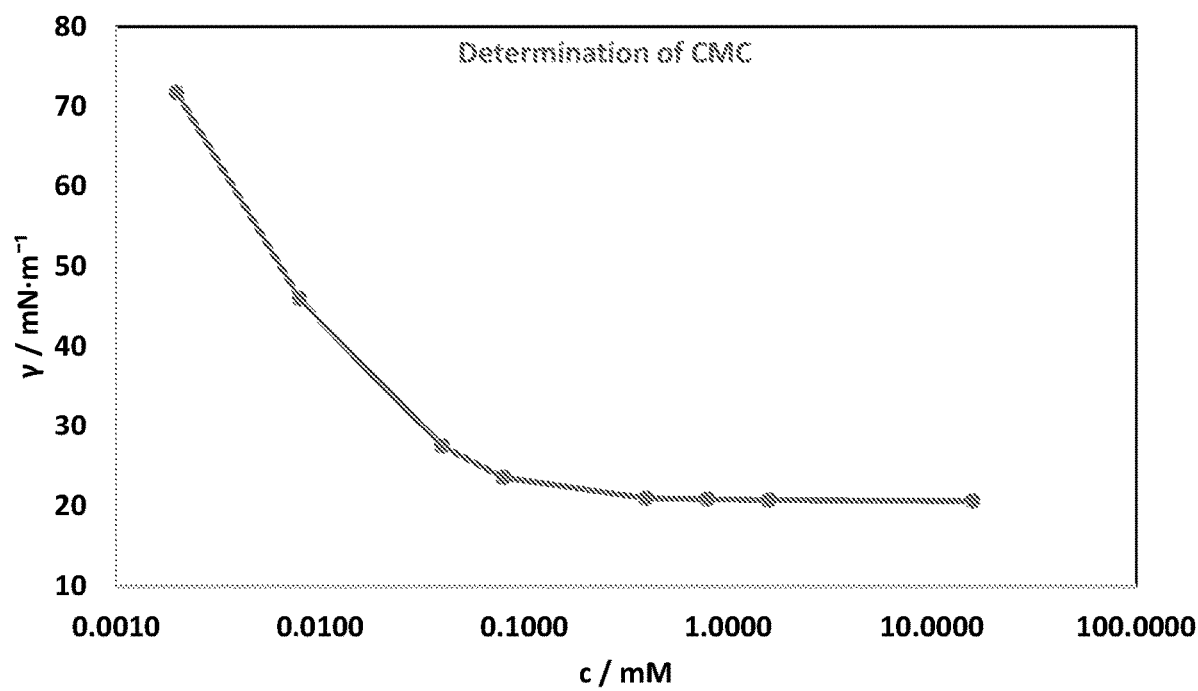
FIG. 6 shows a plot of surface tension versus concentration for Surfactant 5 as described in Example 4b.

The critical micelle concentration (CMC) for Surfactant 5 was measured. From the surface tension change with concentration in water, the CMC was determined to be about 0.39 mmol. The plateau value of minimum surface tension that can be reached by this surfactant is about 21 mN/m, indicating that the surfactant has outstanding interfacial activity. These results are plotted as surface tension versus concentration in FIG. 6.

Figure 7:
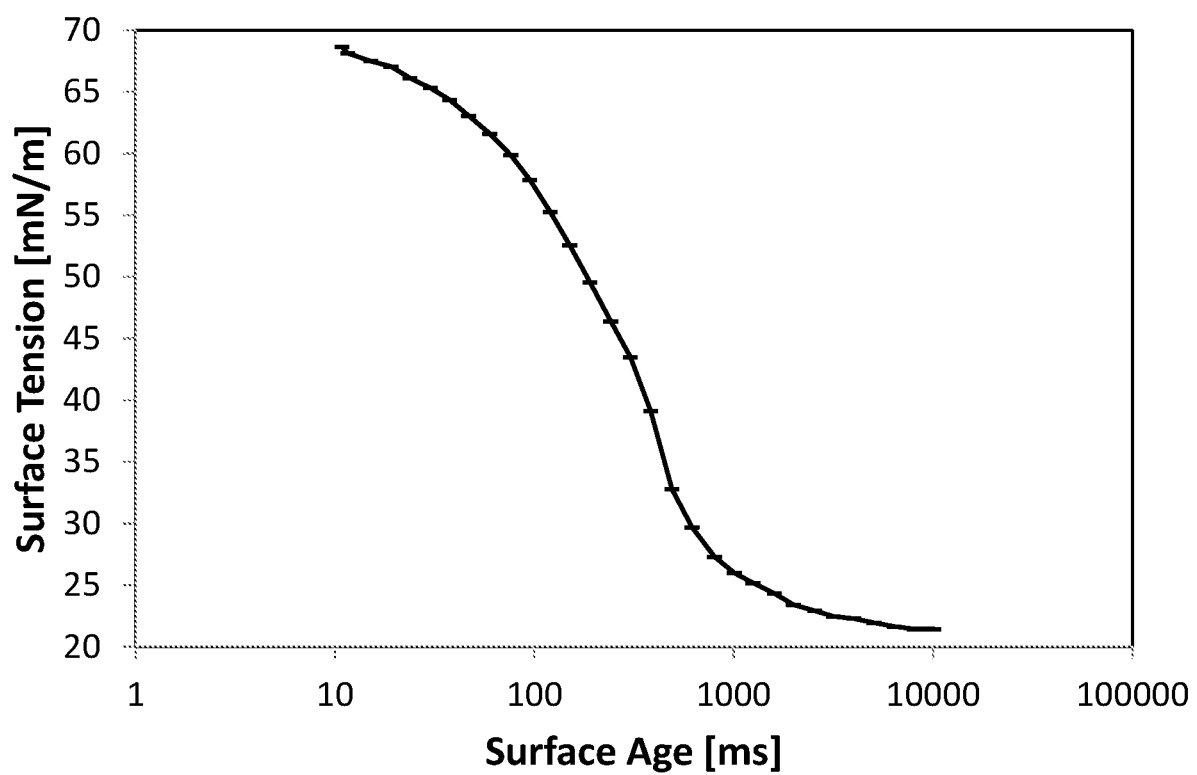
FIG. 7 shows a plot of dynamic surface tension as change in surface tension versus time for Surfactant 5 as described in Example 4b.

The dynamic surface tension of Surfactant 5 was determined with a bubble pressure tensiometer. FIG. 7 shows a plot of the results as surface tension versus time and demonstrates that Surfactant 5 fully saturated a freshly created air-water interface in one second or less, making it fast in terms of interfacial adsorption.

Finally, a solution of Surfactant 5 in water at a concentration of 10×CMC exhibits a 0° contact angle on hydrophobic substrates such as polyethylene and polypropylene, and 10.2° on oleophobic and hydrophobic substrates such as Teflon. These contact angles are extremely low in comparison with the contact angle of water on the same substrate (Table 4).

TABLE 4

| Substrate | CA of Surfactant 5 (°) | Concentration | CA of water (°) |
|---|---|---|---|
| Teflon | 10.2 | 10x CMC | 119 |
| Polyethylene | 0 | 10x CMC | 91.5 |
| Polypropylene | 0 | 10x CMC | 93.3 |
| Polyethylenterephthalate | 0 | 10x CMC | 65.3 |
| Nylon | 0 | 10x CMC | 50 |
| Polyethylene-HD | 0 | 10x CMC | 93.6 |

Example 5

Formulation for Shampoo

In this Example, a formulation for use as a shampoo is provided. This formulation is useful in in providing hair with a smooth and silky feel. The components of the formulation are shown below in Table 5. Additionally, the formulation may include other natural oils and ingredients, as well as vitamins for consumer appeal, in an amount of less than 1 wt. %.

TABLE 5

| Component | Function | Weight % |
|---|---|---|
| Surfactant 5 | Surfactant | 0.1-10 |
| Ammonium lauryl sulfate | Foaming agent | 10-25 |
| Cocamidopropyl betaine | Co-surfactant | 0.1-5 |
| Cocamide diethanolamine | Foam booster | 1-4 |
| Xanthan gum or acrylate copolymer | Thickener/rheology modifier | 0-5 |
| Citric acid | pH stabilizer | 0.1-0.3 |
| Fragrance | | 0.02-0.1 |
| Water | | 49.5-89 |

Example 6

Formulation for Hair Conditioner

In this Example, a formulation for use as a hair conditioner is provided. This formulation may be used to replace or reduce polyquaternium-10, polyquaternium-7 and dimethicone oils, while preserving the easy combability and silky-soft feel that hair conditioners provide. The formulation is shown below in Table 6.

TABLE 6

| Component | Function | Weight % |
|---|---|---|
| Surfactant 3 | Surfactant | 1-10 |
| Surfactant 5 | Surfactant | 0.1-10 |
| Sodium cumene sulfonate | Hydrotrope | 1-3 |
| Ammonium lauryl sulfate | Surfactant | 0.1-6 |
| Ammonium laureth-3 sulfate | Surfactant | 0.1-6 |

TABLE 6-continued

| Component | Function | Weight % |
|---|---|---|
| Cocamide diethanolamine | Foaming agent | 0.5-2 |
| PEG-55 propylene glycol oleate | Emulsifier | 0.01-1 |
| Fragrance | | 0.02-0.1 |
| Water | | 61.9-97.2 |

Example 7

Formulation for Cleanser

In this Example, a formulation for use as a cleanser is provided. This formulation may be used to clean skin and remove make-up. The fatty component, such as a liquid oil, may aid in the removal of oily make-up. The formulation is shown below in Table 7.

TABLE 7

| Component | Function | Weight % |
|---|---|---|
| Non-ionic Surfactant | Surfactant | 15-30 |
| Non-ionic Surfactant | Co-Surfactant | 1-15 |
| Fatty Component | Cleanser | 10-40 |
| Water-soluble Alcohol | Solvent | 10-40 |
| Water-soluble Polyol | Solvent | 10-30 |
| Water-soluble Polymer | Rheology modifier | 0.05-1.0 |
| Inorganic or Organic Salt | Increase hydrophobicity | 0.001-2.0 |
| Fragrance | | 0.0-0.1 |
| Water | | 53.9-99.0 |

Example 8

Formulation for Mascara

In this Example, a formulation for use as a mascara is provided. This formulation may be used to clean skin and remove make-up. The fatty component, such as a liquid oil, may aid in the removal of oily make-up. The formulation is shown below in Table 8.

TABLE 8

| Component | Function | Weight % |
|---|---|---|
| Surfactant | Emulsifier | 0.3-5 |
| Surfactant | Co-Emulsifier | 3-15 |
| Viscosity Increasing Agent | Rheology Modifier | 0.2-1.5 |
| Polymer | Film Forming Agent | 7-25 |
| Polymer | Co-Film Forming Agent | 0.2-5 |
| Pigments | | 1-40 |
| Water | | 30-70 |

Example 9

Formulation for Toothpaste

In this Example, a formulation for use as a toothpaste is provided. The formulation is shown below in Table 9.

TABLE 9

| Component | Function | Weight % |
|---|---|---|
| Surfactant | Stabilizer | 1.0-1.4 |
| Calcium Carbonate | Abrasive | 38-44 |
| Sodium Monofluorophosphate | Oral Care Agent | 0.9-1.3 |

TABLE 9-continued

| Component | Function | Weight % |
|---|---|---|
| Amino Acid | Oral Care Agent | 1-5 |
| Flavoring Agent | | 0.1-2 |
| Water | | 46.3-59.0 |

ASPECTS

Aspect 1 is a formulation for a shampoo, comprising: at least one surfactant of Formula I,

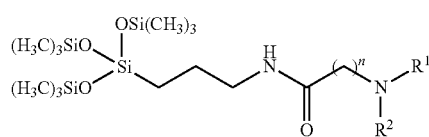

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a foaming agent; and water.

Aspect 2 is the formulation of Aspect 1, further comprising a foam booster.

Aspect 3 is the formulation of any of either Aspect 1 or Aspect 2, further comprising at least one thickener.

Aspect 4 is the formulation of any of Aspects 1-3, further comprising a pH stabilizer.

Aspect 5 is the formulation of any of Aspects 1-4, further comprising a soil penetration agent.

Aspect 6 is the formulation of any of Aspects 1-5, further comprising a fragrance.

Aspect 7 is a formulation for a shampoo, comprising: at least one surfactant of Formula I,

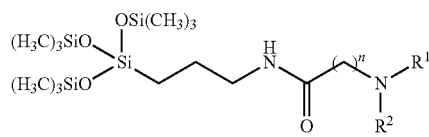

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a thickener; and water.

Aspect 8 is the formulation of Aspect 7, further comprising a foam booster.

Aspect 9 is the formulation of any of either Aspect 7 or Aspect 8, further comprising a pH stabilizer.

Aspect 10 is the formulation of any of Aspects 7-9, further comprising a soil penetration agent.

Aspect 11 is the formulation of any of Aspects 7-10, further comprising a fragrance.

Aspect 12 is a formulation for a hair conditioner, comprising: at least one surfactant of Formula I,

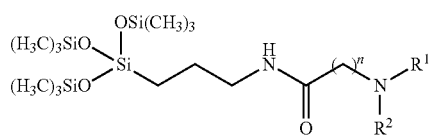

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a fatty component; and water.

Aspect 13 is the formulation of Aspect 12, further comprising an emulsifier.

Aspect 14 is the formulation of either Aspect 12 or Aspect 13, further comprising at least one thickening agent.

Aspect 15 is the formulation of any of Aspects 12-14, further comprising a foaming agent.

Aspect 16 is the formulation of any of Aspects 12-15, further comprising at least one clay.

Aspect 17 is the formulation of any of Aspects 12-16, further comprising a fragrance.

Aspect 18 is a formulation for a cleanser, comprising: at least one surfactant of Formula I,

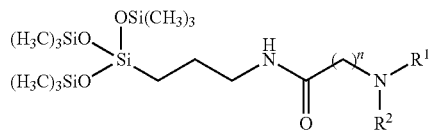

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one solvent; and water.

Aspect 19 is the formulation of Aspect 18, further comprising at least one water-soluble polymer.

Aspect 20 is the formulation of either Aspect 18 or Aspect 19, further comprising at least one water-soluble solvent.

Aspect 21 is the formulation of any of Aspects 18-20, further comprising at least one fatty component.

Aspect 22 is the formulation of any of Aspects 18-21, further comprising at least one conditioner.

Aspect 23 is the formulation of any of claims 18-22, further comprising a hydrophobicity modifier.

Aspect 24 is a formulation for a cleanser, comprising: at least one surfactant of Formula I,

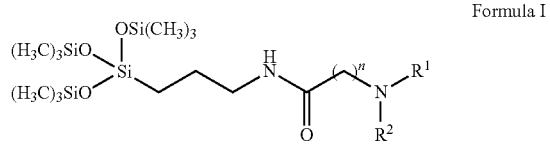

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a humectant; and water.

Aspect 25 is the formulation of Aspect 24, further comprising at least one water-soluble polymer.

Aspect 26 is the formulation of either Aspect 24 or Aspect 25, further comprising at least one water-soluble solvent.

Aspect 27 is the formulation of any of Aspects 24-26, further comprising at least one fatty component.

Aspect 28 is the formulation of any of Aspects 24-27, further comprising at least one conditioner.

Aspect 29 is the formulation of any of Aspects 24-28, further comprising a hydrophobicity modifier.

Aspect 30 is the formulation of any of Aspects 24-29, further comprising at least one solvent.

Aspect 31 is a formulation for a mascara, comprising: at least one surfactant of Formula I,

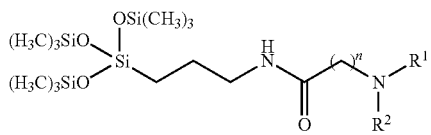

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one polymer; and water.

Aspect 32 is the formulation of Aspect 31, further comprising at least one fatty component.

Aspect 33 is the formulation of either Aspect 31 or Aspect 32, further comprising at least one rheology modifier.

Aspect 34 is the formulation of any of Aspects 31-33, further comprising at least one emulsifier.

Aspect 35 is the formulation of any of Aspects 31-34, further comprising a pigment.

Aspect 36 is a formulation for a toothpaste, comprising: at least one surfactant of Formula I,

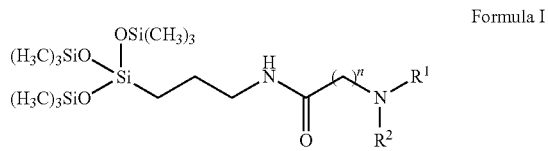

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; a fluoride ion source; and water.

Aspect 27 is the formulation of Aspect 26, further comprising at least one basic amino acid.

Aspect 28 is the formulation of either Aspect 36 or Aspect 37, further comprising calcium carbonate.

Aspect 29 is the formulation of any of claims 36-38, further comprising a flavoring agent.

The invention claimed is:
1. A formulation for a shampoo, comprising:
at least one surfactant of Formula I,

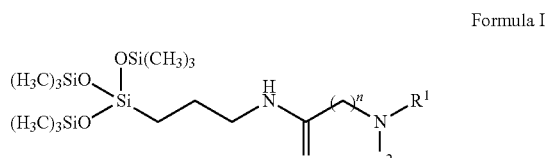

Formula I wherein $R^1$ and $R^2$ may be the same or different, and comprise at least one group selected from the group consisting of a $C_1$-$C_6$ alkyl chain, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;
- n is an integer from 3 to 12;
- the terminal nitrogen is optionally further substituted with $R^3$, wherein $R^3$ is selected from the group consisting of hydrogen, oxygen, hydroxyl, and $C_1$-$C_6$ alkyl;
- an optional counterion associated with the surfactant which, if present, is selected from the group consisting of chloride, bromide, and iodide;

at least one of a foaming agent and a thickener; and
water.

2. The formulation of claim 1, further comprising a foam booster.

3. The formulation of claim 1, further comprising a pH stabilizer.

4. The formulation of claim 1, further comprising a soil penetration agent.

5. The formulation of claim 1, further comprising a fragrance.

6. A formulation for a hair conditioner, comprising:
at least one surfactant of Formula I,

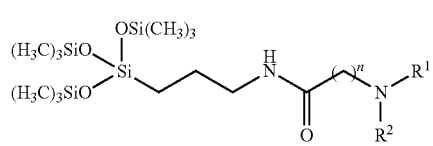

Formula I wherein $R^1$ and $R^2$ may be the same or different, and comprise at least one group selected from the group consisting of a $C_1$-$C_6$ alkyl chain, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;
- n is an integer from 3 to 12;
- the terminal nitrogen is optionally further substituted with $R^3$, wherein $R^3$ is selected from the group consisting of hydrogen, oxygen, hydroxyl, and $C_1$-$C_6$ alkyl;
- an optional counterion associated with the surfactant which, if present, is selected from the group consisting of chloride, bromide, and iodide;
- a fatty component; and
water.

7. The formulation of claim 6, further comprising an emulsifier.

8. The formulation of claim 6, further comprising at least one thickening agent.

9. The formulation of claim 6, further comprising a foaming agent.

10. The formulation of claim 6, further comprising at least one clay.

11. The formulation of claim 6, further comprising a fragrance.

12. A formulation for a cleanser, comprising:
at least one surfactant of Formula I,

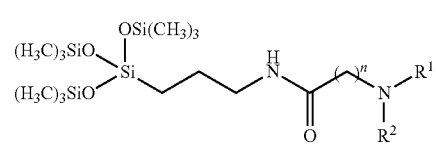

Formula I wherein $R^1$ and $R^2$ may be the same or different, and comprise at least one group selected from the group consisting of a $C_1$-$C_6$ alkyl chain, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;
- n is an integer from 3 to 12;
- the terminal nitrogen is optionally further substituted with $R^3$, wherein $R^3$ is selected from the group consisting of hydrogen, oxygen, hydroxyl, and $C_1$-$C_6$ alkyl;
- an optional counterion associated with the surfactant which, if present, is selected from the group consisting of chloride, bromide, and iodide;
- at least one of a solvent and a humectant; and
water.

13. The formulation of claim 12, further comprising at least one water-soluble polymer.

14. The formulation of claim 12, further comprising at least one fatty component.

15. The formulation of claim 12, further comprising at least one conditioner.

16. The formulation of claim 12, further comprising a hydrophobicity modifier.

17. A formulation for a toothpaste, comprising:
at least one surfactant of Formula I,

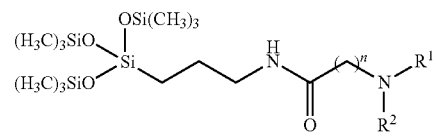

Formula I wherein $R^1$ and $R^2$ may be the same or different, and comprise at least one group selected from the group consisting of a $C_1$-$C_6$ alkyl chain, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;
- n is an integer from 3 to 12;
- the terminal nitrogen is optionally further substituted with $R^3$, wherein $R^3$ is selected from the group consisting of hydrogen, oxygen, hydroxyl, and $C_1$-$C_6$ alkyl;
- an optional counterion associated with the surfactant which, if present, is selected from the group consisting of chloride, bromide, and iodide;
a fluoride ion source; and
water.

18. The formulation of claim 17, further comprising at least one basic amino acid.

19. The formulation of claim 17, further comprising calcium carbonate.

20. The formulation of claim 17, further comprising a flavoring agent.

* * * * *